United States Patent
Wu et al.

(10) Patent No.: US 7,696,474 B2
(45) Date of Patent: Apr. 13, 2010

(54) METHODS AND APPARATUS OF ION MOBILITY SPECTROMETER

(75) Inventors: Ching Wu, Acton, MA (US); Leslie Bromberg, Sharon, MA (US)

(73) Assignee: Excellims Corporation, Acton, MA (US)

( * ) Notice: Subject to any disclaimer, the term of this patent is extended or adjusted under 35 U.S.C. 154(b) by 240 days.

(21) Appl. No.: 12/026,192

(22) Filed: Feb. 5, 2008

(65) Prior Publication Data

US 2008/0210861 A1 Sep. 4, 2008

Related U.S. Application Data

(60) Provisional application No. 60/888,172, filed on Feb. 5, 2007.

(51) Int. Cl.
*H01J 49/42* (2006.01)
*H01J 49/26* (2006.01)
*H01J 49/10* (2006.01)

(52) U.S. Cl. .................. 250/281; 250/282; 250/288; 250/287; 250/423 R; 250/424

(58) Field of Classification Search ............... 250/281, 250/282, 288, 287, 423 R, 424
See application file for complete search history.

(56) References Cited

U.S. PATENT DOCUMENTS

| | | | |
|---|---|---|---|
| 6,107,628 A | 8/2000 | Smith | |
| 6,481,263 B1 | 11/2002 | Haley | |
| 6,690,004 B2 | 2/2004 | Miller | |
| 6,727,495 B2 * | 4/2004 | Li | |
| 7,045,778 B2 * | 5/2006 | Guevremont et al. | 250/288 |
| 7,385,187 B2 * | 6/2008 | Verentchikov et al. | 250/287 |
| 7,547,878 B2 * | 6/2009 | Schultz et al. | 250/282 |
| 7,547,879 B2 * | 6/2009 | Miller et al. | 250/286 |
| 2005/0109930 A1 | 5/2005 | Hill | |
| 2005/0178964 A1 | 8/2005 | Guevremont | |
| 2005/0205775 A1 | 9/2005 | Bromberg | |
| 2006/0192102 A1 | 8/2006 | Miller | |
| 2007/0084999 A1 | 4/2007 | Miller | |
| 2008/0169417 A1 | 7/2008 | Cohn | |

FOREIGN PATENT DOCUMENTS

WO    WO2006/114580 A1    11/2006

\* cited by examiner

*Primary Examiner*—Nikita Wells

(57) ABSTRACT

The present invention describes apparatuses and methods that provide energy to ions in a non-thermal manner. The elevated ion energy minimizes or eliminates interferences due to clustering with polar molecules, such as water. The energized ions are separated in an ion mobility spectrometer. During the ion transportation and separation process, the elevated energy level of ions prevents them from clustering with neutral molecule inside the spectrometer. The additional electric field component only causes ions to reach elevated energy level, whereby the spectrometer can preserve its normal performance, meanwhile avoiding interference from water and other neutral molecules. A RF electric field is applied to the ions in ionization, reaction and separation region of ion mobility spectrometers.

43 Claims, 19 Drawing Sheets

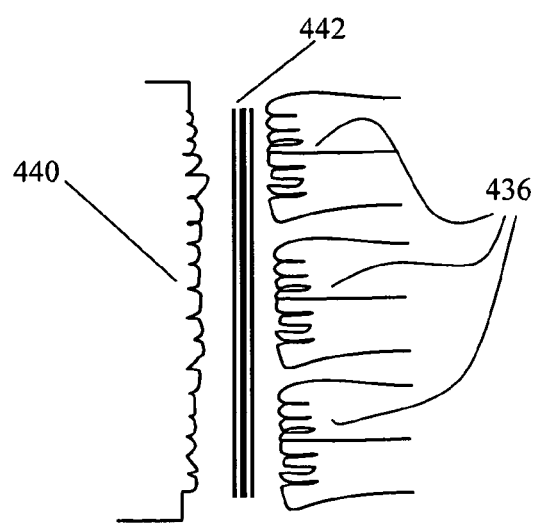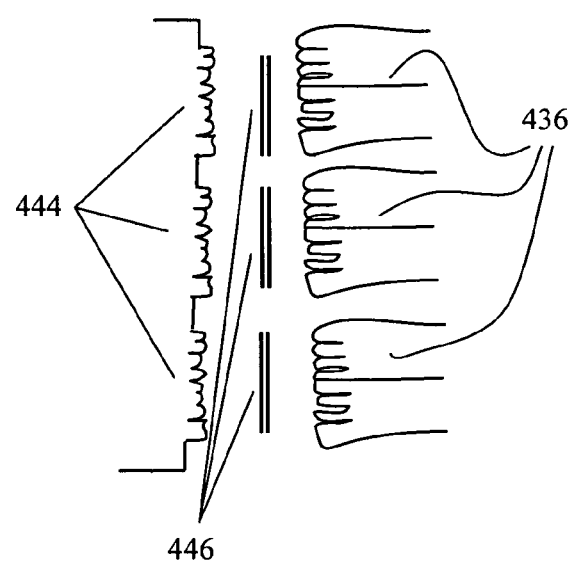
Figure 4a                    Figure 4b

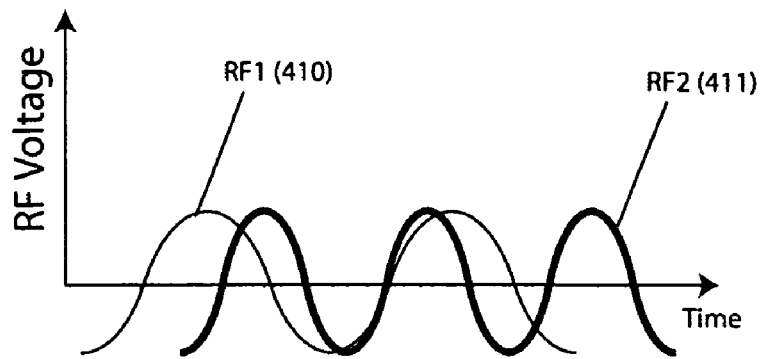
Figure 10c
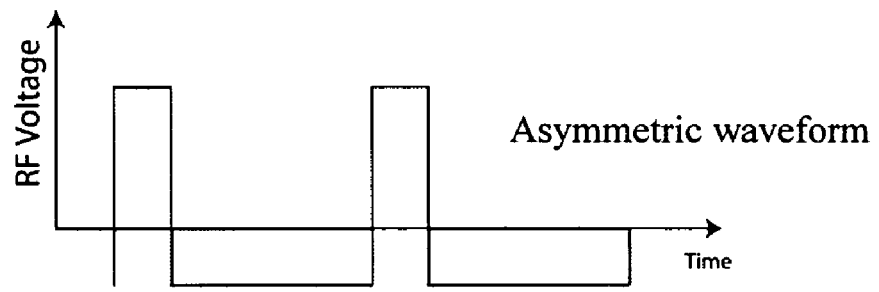
Asymmetric waveform
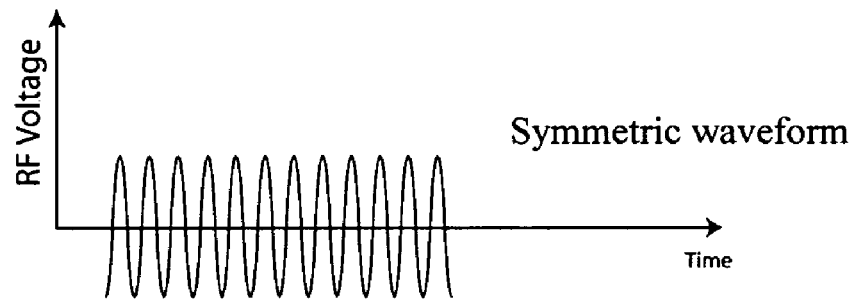
Symmetric waveform
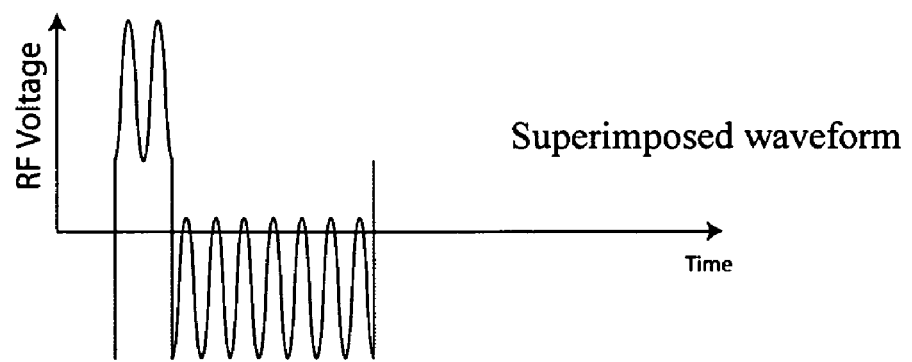
Superimposed waveform
Figure 10d

METHODS AND APPARATUS OF ION MOBILITY SPECTROMETER

CROSS-REFERENCE TO RELATED APPLICATIONS

The present application claims the benefit of and priority to corresponding U.S. Provisional Patent Application No. 60/888,172, filed Feb. 5, 2007 respectively, the entire content of the application is herein incorporated by reference.

BACKGROUND OF THE INVENTION

Ion mobility spectrometers (IMS) are widely used in field chemical analysis. IMS separate ionic species based on their ion mobility in a given media (either gas or liquid). Recent development of the IMS technology results in two forms of IMS instruments and systems. The time-of-flight (TOF) IMS separate ions based on their steady state ion mobilities under constant electric field. High resolving power with IMS has been achieved with the TOF-IMS instruments. Alternatively, devices that separate ions based their mobility changes under high field conditions, such as field asymmetric ion mobility spectrometer (FAIMS) or differential mobility spectrometer (DMS), can also be used. These devices separate the ions through the use of nonlinear mobility, which occurs at high values of normalized electric field (E/n). The normalized electric field refers to the relation between the applied electric field at a given location in space divided by the neutral particle number density. The normalized electric field is a key parameter in ionized gases and plasmas, as the energy of ionized particles, the breakdown and sustaining voltages and other key parameters depend upon this ratio. The FAIMS and/or DMS devices have sensitivity and selectivity that are still substantially worse (less) than linear drift tubes.

In many cases, in a less-than ideal operating environments (in particular those with high humidity or other site-specific interferences), the spectrometer performance is significantly limited. The performance of the ion mobility spectrometers in these circumstances can be improved by increasing the temperature of the gas. High temperature ion mobility spectrometers are common in applications that require high resolution analysis, such as explosive detection. Unfortunately, the use of high temperature drift tubes in IMS devices results in high power consumption, limited portability and other operational disadvantages, including slow turn-on from cold conditions. In addition, dry drift gas is often required in these spectrometers. A dehumidifier in front of the unit has been used to address these problems (either as a water absorber or as a hydrophobic membrane) with significant trade-offs. The volume and weight, as well as the need for regeneration, makes the use of dehumifier cell impractical, while the use of the hydrophobic membrane decreases the volume/amount of the sample that is introduced into the device, decreasing its sensitivity.

SUMMARY OF THE INVENTION

The present invention generally relates to systems and methods for transmitting additional energy to ions in the ion mobility spectrometer that results in non-thermal equilibrium. The apparatus is referred to as Elevated Energy Ion Mobility Spectrometer (EE-IMS). In an EE-IMS, the ion energy can be increased non-thermally through the ionization region, the ion chemistry interaction (reaction) region, and/or the separation region of ion mobility spectrometers. In one aspect, the elevated energy level of ions prevents them from clustering with neutral molecules inside the spectrometer.

In one embodiment of the present invention, the additional electric field component causes ions to move only in the direction that is perpendicular to the normal drift direction in a time of flight type ion mobility spectrometer (TOFIMS), whereby the spectrometer can preserve its normal performance (e.g. resolution), meanwhile avoiding interference from water and other neutral molecules. In this embodiment, the fundamental difference from the EE-IMS and other ion mobility spectrometers and field asymmetric ion mobility spectrometer combinations are: (a) The present invention does not cause analytical ion separation with AC field; the AC electric field component can normally be symmetric or any waveform that may cause ions to stay in a elevated energy level. The frequency of the waveform may be in a broad range of RF, e.g. in 0.1-10 MHz or ever in the Microwave range; (b) Ions in a EE-IMS substantially stay at high energy level compared to FAIMS or DMS where ions partially stay at low energy level. (c) There is no effect of gas flow on ion separation; the conventional counter gas flow in a TOFIMS is used for drift tube cleaning only. It does not serve as ion carrier or a balancing force used for ion separation; and (d) the analytical ion separation is only in the drift axis direction based on the steady state mobility of ions. In this application, the terms AC and RF are used interchangeably.

This invention describes an apparatus and method that supplies energy to the ions in an ion mobility separator that results in a non-thermal equilibrium distribution between the ions and the background gas molecule. In one non-limiting example, the drift tube guard rings are made of multiple electrodes in order to apply a waveform that is perpendicular to the ion drifting direction, and are referred to as segmented guard electrodes. As ions travel in an IMS along the axis of a drift tube under influence of an applied DC electric field, an AC electric field is applied in the second direction that perpendicular to the ion drift direction, the high velocity movement under the second field cause ions to stay at higher energy level while drifting in the IMS. As a result, ions under the elevated energy level are free from clustering with neutral molecules in the spectrometer, or their clustering tendencies are reduced. The AC electric field can be applied also in the ionization region, in the ion chemistry reaction region, as well as in the ion separation (drift) region.

In some embodiments of the present invention, the energy source that supplies non-thermal energy to the ions is a radio frequency (RF) electric field. Therefore, an EE-IMS uses RF electric field to heat up ions non-thermally. Non-thermally means that the ion energy is NOT in equilibrium with the background gas. The increased energy of the ions provides a means to modify the linear drift mobility in order to minimize the problems with TOFIMS. The EE-IMS of the invention uses high RF electric fields in order to increase the effective temperature of the ions, in one aspect to minimize the adverse chemical and physical behavior of the ions due to humidity or other interferences in the environment. It may also use a combination of DC fields and RF fields, such that the ion separation is performed using the DC field, but the RF fields are used to modify the chemistry and prevent some of the problem associated with present day devices.

Alternatively, the RF heating method during ion transportation and mobility based separation can be used for FAIMS, DMS and/or other derived forms where the RF electric field is applied in the direction that is perpendicular (or other angles) to the (asymmetric) electric field that causes the ion mobility based separation. In some embodiments, the fundamental differences from the EE-IMS and conventional IMS, including TOFIMS, FAIMS and DMS are that: (1) Ions in a EE-IMS are kept at high effective temperature (high energy) conditions by a RF electric field through the course of ion transportation and mobility based separation. (2) a RF electric field is used to continuously maintain the elevated ion energy and it does not cause analytical ion separation: the RF electric field component can be symmetric as long as it causes the ions to stay in an elevated energy level. (3) In an EE-IMS, there is no effect of drift gas flow on ion separation column: the conventional counter gas flow in TOF-IMS is only used for drift tube cleaning. It does not serve as ion carrier or a balancing force used for ion separation. The ions are separated only in the DC electric field direction based on the steady state mobility of the ions. (4) In an EE-IMS, including EE-FAIMS and/or EE-DMS, the RF field is applied in the direction that is perpendicular (with other angles) to the direction of the conventional asymmetric electric field used to filter out ions in these devices.

BRIEF DESCRIPTION OF THE DRAWINGS

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

FIGS. 4a and 4b show a schematic diagram illustrating RF energization using inductive means, the RF needed to drive the guard electrodes of the instrument in FIGS. 2 and 3;

FIG. 6a uses a single RF power supply, while FIG. 6b uses multiple RF power supplies;

FIG. 10a through 10d show a variety of RF waveforms that is used in prior art and this invention;

DETAILED DESCRIPTION OF VARIOUS EMBODIMENTS

Figure 1:
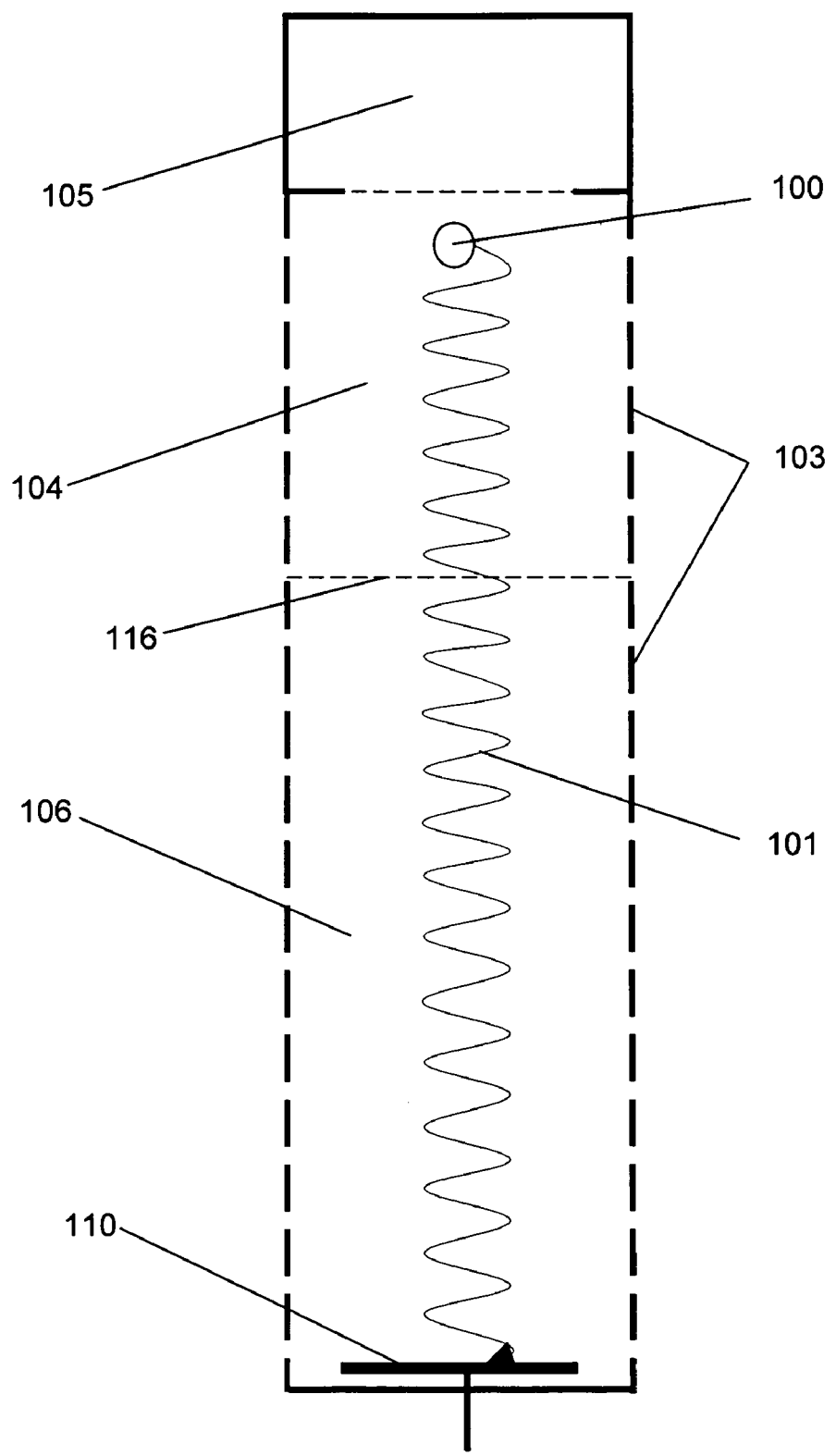
FIG. 1 illustrates an example of ion motion in the EE-IMS, where the ions transport through a drift tube under the influence of both an RF and DC electric fields.

The term ion mobility separator, and ion mobility spectrometer, and ion mobility based spectrometers are used interchangeably in this invention, often referred to as IMS, including time-of-flight (TOF) IMS, differential mobility spectrometers (DMS), field asymmetric ion mobility spectrometers (FAIMS) and their derived forms. A time of flight ion mobility spectrometer and their derived forms refers to, in its broadest sense, any ion mobility based separation device that characterize ions based on their time of flight over a defined distance. A FAIMS, a DMS, and their derived forms separate ions based on their ion mobility characteristics under high values of normalized electric field.

The systems and methods of the present inventions may make use of "drift tubes." The term "drift tube" is used herein in accordance with the accepted meaning of that term in the field of ion mobility spectrometry. A drift tube is a structure containing a neutral gas through which ions are moved under the influence of an electrical field. It is to be understood that a "drift tube" does not need to be in the form of a tube or cylinder. As understood in the art, a "drift tube" is not limited to the circular or elliptical cross-sections found in a cylinder, but can have any cross-sectional shape including, but not limited to, square, rectangular, circular, elliptical, semi-circular, triangular, etc. In many cases, a drift tube is also referred to the ion transportation and/or ion filter section of a FAIMS or DMS device.

Neutral gas is often referred to as a carrier gas, drift gas, buffer gas, etc. and these terms are considered interchangeable herein. The gas is at a pressure such that the mean free path of the ion, or ions, of interest is less than the dimensions of the drift tube. That is the gas pressure is chosen for viscous flow. Under conditions of viscous flow of a gas in a channel, conditions are such that the mean free path is very small compared with the transverse dimensions of the channel. At these pressures the flow characteristics are determined mainly by collisions between the gas molecules, i.e. the viscosity of the gas. The flow may be laminar or turbulent. It is preferred that the pressure in the drift tube is high enough that ions will travel a negligible distance, relative to the longitudinal length of the drift tube, therefore a steady-state ion mobility is achieved.

The phrase "and/or," as used herein in the specification and in the claims, should be understood to mean "either or both" of the elements so conjoined, i.e., elements that are conjunctively present in some cases and disjunctively present in other cases.

Unless otherwise specified in this document the term "particle" is intended to mean chemical and/or biological single or plurality of sub-atomic particle, atom, molecule, large or macro molecule, nanoparticle, or other matters that are vapor, droplets, aerosol, liquid, solid that follow a mobile medium, where the medium can be a gas, a liquid, supercritical fluid and/or other fluidic materials.

The present invention generally relates to systems and methods of using an energy source for supplying energy to the ions for maintaining them at an energy level that is higher than the thermal energy at a given operating temperature. In one set of embodiments, the energy is supplied continuously during ion transportation and/or mobility based separation process, such that the ions energy is always above the thermal energy level. In another set of embodiments, the energy is supplied in a manner such that the ions are prevented from continuously staying at the thermal energy level for substantially greater than 1 μs throughout the ion transportation and/or mobility based separation process.

One aspect of the invention relates to systems and methods for preventing clustering or decreasing the tendency of ions to clustering with surrounding neutral molecules. It is presently understood that high humidity interferes with performance of IMS devices through the mechanism of clustering. The energy associated with clusters is on the order of 200 kcal/mol (for protonated water cluster $H_3O^+$), with lower energies for larger clusters (30-40 kcal/mol for n~2, decreasing with cluster size).

It has been well established that a means of preventing the effects of high humidity on the IMS detectors is by operation of the drift tube at elevated temperature. High temperature operation requires power and limits the transient operation of the device (it requires a substantial period of time for achieving uniform temperature through the instrument). One embodiment of this novel approach described herein involves a method that non-thermally adds additional energy to the ions (i.e., heating them) while maintaining room-temperature of the background gas, and achieving separation through otherwise conventional ion mobility spectrometer. Providing kinetic energy to the ions breaks up the ion-water clusters, minimizing or eliminating the interference due to high humidity and other neutral molecules.

Very high fields are required to totally dissociate the water clusters, but it is relatively easy to provide enough energy to dissociate water clusters $M^+(H_2O)_n$ that have n>1. It is not considered necessary to provide total declustering, and even in instruments with absorbers or membranes low number clustering occurs. The problem associated with high humidity occurs when the clusters are so large that ion chemistry is prevented. Normalized field strengths of a few Townsends (E/n) are required to provide the dissociation energy, resulting in electric fields on the order of 10 kV/cm at atmospheric pressure. With a variety of embodiments in this invention, a certain number of neutral molecules associated with the ions could be controlled by providing certain amount of energy to the ions. Thus, under a given energy level, one kind of ions may remain clustered with a known number of neutral molecules. By adjusting the energy level, the degree of clustering is controlled.

In some embodiments of the present invention, the energy source that supplies non-thermal energy to the ions is a radio frequency (RF) electric field, but is not-limited to only this energy source. The energy source can be tuned to provide a level of energy for the purpose of, but not limited to, controlling the degree of clustering, declustering, controlling the degree of ion-molecular interaction. In some cases the normalized RF electric field is greater than 2 Townsend, or the normalized RF electric field is greater than 40 Townsend, and the RF electric field frequency is between 10 kHz and 2 MHz, or the RF electric field is between 500 MHz and 3 GHz.

The use of high intensity electric fields, which provide energy exclusively to the ions requires very little power, is nearly instantaneous (does not have to wait for instrument warm-up) and has the added benefit that it provides an additional knob that can be used to control the ion chemistry. There is some heating of the background neutrals, as the ions dissipate their energy in the background neutrals, but the heating power associated with this mechanism is very small (<100 microW).

Because linear radio frequency (RF) fields need to go through zero for a short period of time twice each cycle in some applications of the present invention, it is important to raise the frequency in order to minimize the time that the ions hang around during the periods of low electric fields. Time constants of clustering phenoma at atmospheric pressure are on the order of 1 microsecond. Thus, frequencies on the order of several hundred kHz and higher are preferred. One embodiment that can prevent the RF field reducing to zero is using two RF fields that are perpendicular to each other. As these two waveforms have a phase difference as such, when one RF field is reduced to zero the other one is at its maximum. Therefore ions traveling in this superimposed electric field can be maintained at high energy level.

In one set of embodiments, the energy is supplied in a manner such that the ions are prevented from continuously staying at the thermal energy level for greater than substantially 1 μs throughout the ion transportation and/or mobility based separation process. This is achieved by the use of RF electric field frequencies higher than a few hundred kHz. In one non-limiting example, separation and drift is achieved through the use of a low intensity DC the axial direction, while high intensity fields in the direction normal to the low intensity electric field prevent the ions from clustering in the ionization region, in the reaction region, and/or in the drift region of a drift tube. The RF fields are symmetric, as opposed to transverse field IMS such as DMS or FAIMS devices (FIG. 9), which use asymmetric RF fields (FIG. 10a) for separating the ions through non-linear mobility. FIG. 1 shows schematically the ion motion trajectory 101 of a ion 100 under influence of the combined DC and RF electric fields in the drift section 106 and in the chemical interaction (reaction) region 104. For clarity in FIG. 1, the additional elements shown are: a series of guard electrodes 103 define the electric fields in the drift tube, a ionization source 105 that generate primary ions, a energizing gate 116, and a ion detector 110. The oscillatory drift maybe more pronounced than what is shown in FIG. 1 and the ion motion may experience more oscillations during the travel that what is depicted, therefore the relative distance of the ion travel in the RF field would be a very small fraction of the typical cross-section dimension of the IMS.

Figure 2:
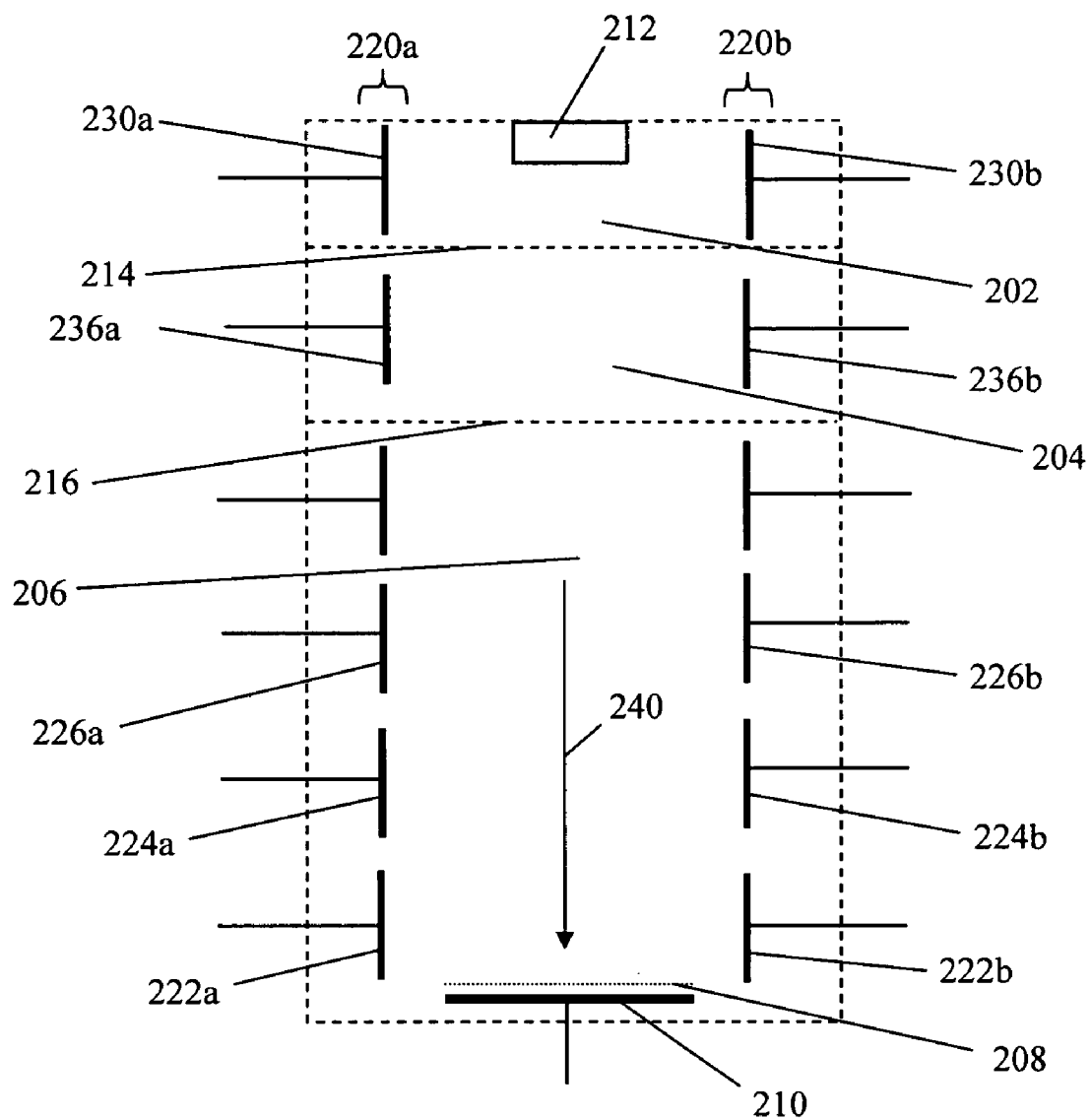
FIG. 2 shows a schematic diagram of the EE-IMS in TOFIMS using electrodes that are biased with both DC and RF fields.

FIG. 2 shows a schematic diagram of the EE-IMS in time of flight ion mobility spectrometer using electrodes that are biased with both DC and RF fields. A narrow swarm of ions are introduced into the drift region 206, which serves to separate ionic species on the basis of their steady state ion mobilities. Ions of one polarity created in ionization region 202 by ionization source 212 are separated from the other polarity ions by application of DC field by appropriate biasing of field separator grid (gate) 214. The ionization source 212 can be a radioactive source, a photoionization source, a corona source, electrospray ionization source or any means to generate ions of both polarities from the neutral gas in the ionization region 202. In many cases, the combination of 212, 202 and other surrounding elements are collectively referred to as ionization source. These ions (mainly primary ions, or reactant ions), enter chemical interaction region 204 where they interact with the sample that is introduced into device through a sample feed, not shown in FIG. 2. The sample may also be introduced into the ionization chamber region 202. Ions of one or both polarities are moved to chemical interaction region 204, passing through a gate 214. As an alternative embodiment, regions 202 and 204 may be combined. RF electric fields can be generated in the reaction region of the drift tube by either adding RF electric fields to the DC field through energizing gates 214 or 216 or segmented guard electrodes 236a and 236b. The RF field can be add to the ionization chamber through energizing the segmented guard electrodes 230a and 230b or energizing gate 214 and source element 212. The purpose of the reaction region 204 is for ion chemistry to develop to the point where steady state distribution is reached between the reaction ions, the product ions and the gas molecules present in the reaction region 204, which includes the sample molecules. The ion gate 216 introduces an ion cloud of short duration into the drift region 206, which under the action of DC field drift the sample ions separate according to their linear mobility under a constant electric field. After separation by mobility, ions are collected by ion detector electrode 210 which is shielded by aperture grid 208. The operation of conventional ion mobility spectrometers with linear tubes is described, but the present invention is not limited to this format. For example, the EE-IMS system and method can be repeated for one or more additional drift dimensions. The segmented guard electrodes 220a and 220b are biased with a combination of DC fields and RF fields. A voltage ladder is such that the DC bias of electrode 222a is that same as that of 222b, 224a is that same as that of 224b, 226a is that same as that of 226b, and so forth. Thus the DC fields establish a uniform field in the drift region 206, appropriate for ion separation, and provide adequate bias in the ionization chamber region 202 and reaction region 204. The voltage distribution however, is such that electrode 222a has a RF field that differs by 180 degrees (i.e., by polarity) from that of 222b, that electrode 222b different by 180 degrees from 224b, and so forth.

It is possible to use strong RF electric fields also in the ionization region and/or in the chemical interaction region. Ideally ion chemistry would result in a large fraction of the charges in ions of the species that are being identified. Because of high electron affinity and proton affinity of the species of interest in mobility spectrometers, charges under normal conditions attach preferentially to these species, resulting in instruments that are very sensitive to these species. Clustering under adverse conditions can prevent ion chemistry to develop, which would severely degrade or even prevent detection of these species. By providing high energy reactive ions the clustering is minimized and the ion chemistry can proceed. The strong RF fields can be generated by RF voltages applied directly to the gates 214 and 216, and to the ionization source 212, or to segmented guard electrodes 230a-230b, 236a-236b.

The axial separation 240 is achieved due to the DC field in a time-of-flight cell 206, as in conventional TOFIMS devices. Resolution should be comparable or better to that of conventional IMS devices, but sensitivity could be much increased (maybe ~2 orders of magnitude higher) due to the absence of the membrane, which decreases the introduction of the sample into the spectrometer.

In this non-limiting example, the differences between the EE-IMS device and other transverse field IMS (FAIMS or DMS) are: (a) Ion separation is through linear drift tubes, not through asymmetric RF fields. (b) Ion declustering is achieved through high intensity RF fields. (c) Relatively slow gas motion (mainly needed for drift tube cleaning) is required that should not impact instrument resolution.

In some embodiments, the method for separating ions comprises: introducing ions into an ion mobility based spectrometer, transporting and/or separating ions while supplying energy to the ions maintaining them at an energy level that is higher than the thermal energy at a given operating temperature, and preventing ions from continuously staying at the thermal energy level for substantially greater than 1 μs throughout the transportation and/or separation process. The energy level can be controlled/or adjusted to different levels for a sequence of ion mobility measurements. The method can also comprise the step of preventing or decreasing ions from clustering with surrounding neutral molecules. In addition, the method can comprise the step of preventing or decreasing ions from clustering with surrounding neutral molecules in the ionization region and/or the chemical reaction regions. Whereby, the energy is provided by a RF electric field. In some cases, the RF electric fields operate at the same frequency from different sources, and/or in other cases, the RF electric fields are substantially uniform in space by the use of multiple segmented guard electrodes driven with waveforms that have been phase shifted with respect to one another.

Figure 3:
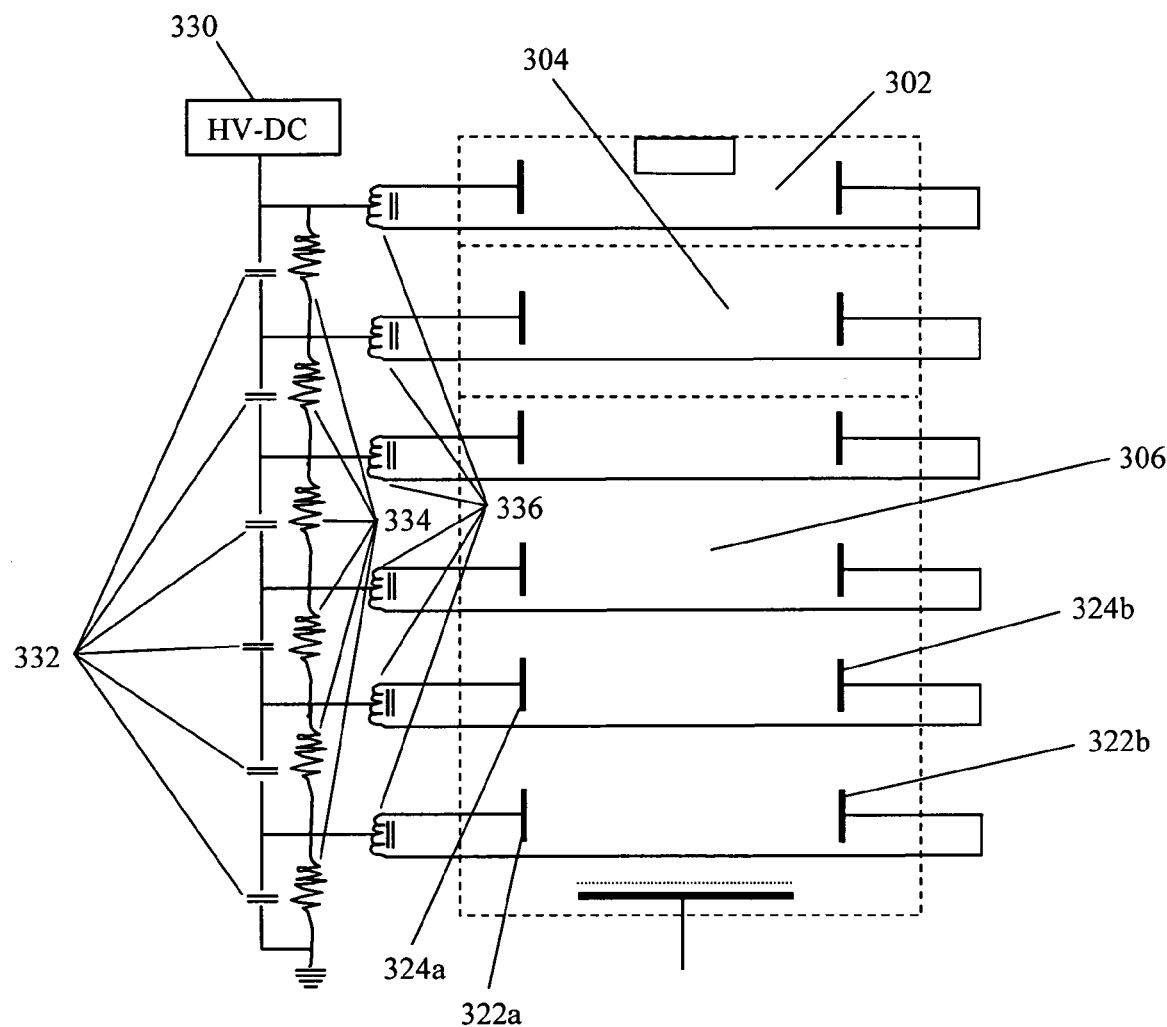
FIG. 3 shows a schematic diagram of the novel instrument showing one aspect of the invention with the use of inductive drive to generate the multiple RF field.
Figure 5A:
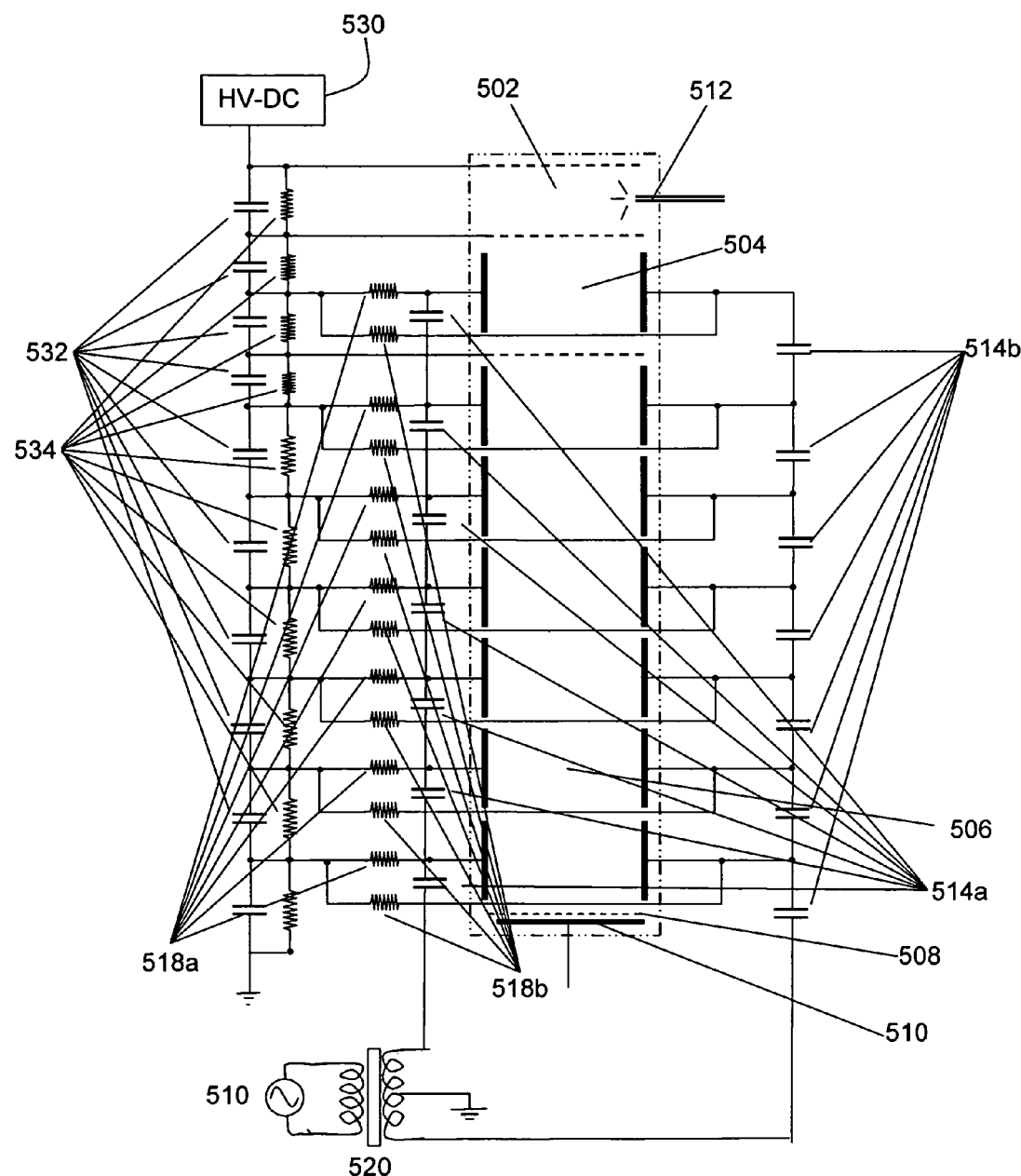
FIGS. 5a and 5b show an embodiment of the novel instrument showing one aspect of the invention with the use of capacitive drive to generate the multiple RF field.
Figure 5B:
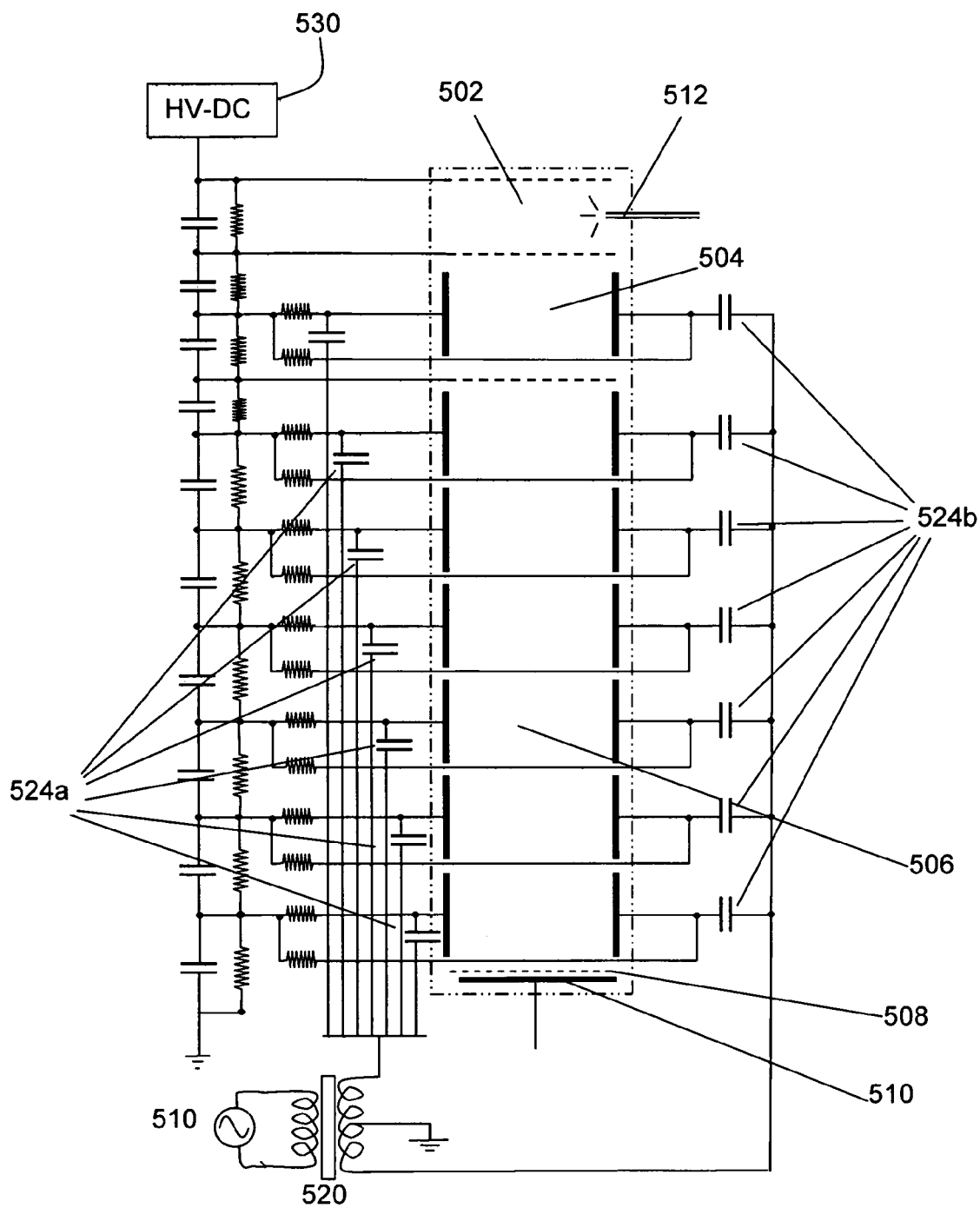

In a variety of embodiments, three means of generating the multiple RF/DC fields have been described: inductive, capacitive and resonant. One uses inductive coupling to provide the RF field on a DC bias and is shown in FIG. 3. Another uses capacitive coupling to provide the DC bias field on a RF field and is shown in FIGS. 5a and 5b. FIG. 3 shows a schematic of the electrical system to drive the electrodes 220a-220b described in FIG. 2. High voltage power supply 330 is used to generate a voltage ladder that results in uniform DC field distribution in drift chamber 306, and appropriate field distribution in reaction region 304 and ionization chamber 302. The high voltage is divided by the use of a capacitor/resistor ladder made from capacitor ladder 332 and resistor ladder 334. Note that in the absence of RF fields in the RF windings, the opposite electrodes 322a and 322b, 324a and 324b, and so forth, are at the same potential. RF is applied to the primary of a core at the appropriate magnitude and frequency. The multiple windings 336 are wound as independent secondaries in what in principle is the same core. Alternatively, multiple cores could be used, with the primaries going through the entire core.

With respect to FIG. 3, both electrode ladders are biased using high voltage DC power supply 330. The segmented guard electrodes are sequentially biased through the use of a DC voltage ladder that includes a capacitive ladder 332 and a resistive ladder 334. Secondary windings of one or multiple transformers, as will be described below, are used to generate the multiple RF fields required for energizing the coupled electrode pairs. The inductive coupling will require a single ferrite transformer, with multiple windings that have a DC bias. This approach minimizes the size and weight of the instrument. Alternatively, a circuit with multiple magnetic cores with a primary winding in series, each with its own secondary winding to drive each section of the device. In the case of FIG. 4a or 4b, the center tap of each secondary winding is attached to the DC bias of the appropriate element of the DC voltage ladder, while the opposite leads are attached to the coupled segmented guard electrodes. A large number of AC voltages need to be generated in order not to short out the DC bias, FIGS. 4a-4b shows means of generating the multiple voltages (capable of operating at different DC biases). In FIG. 4a, there is a single primary winding 440, with secondary windings 436 around a single core 442. In FIG. 4b, there are multiple cores 446, and the primary winding 444 of each core is driven in series. FIGS. 4a and 4b show common center tap for the secondary, which can be connected to the DC bias (not shown in FIG. 3). In FIG. 4b all the windings are driven by the same signal, but this does not have to be the case.

FIGS. 5a-5b shows means of providing the AC energization through capacitive means. For illustration purposes, in FIGS. 5a and 5b electrospray ionization source 512 is used as the ionization source, as well as an ionization region 502, a chemical interaction region 504, a drift region 506, a collector aperture 508, a ion detector 510 and a high voltage power supply 530. The capacitive and resistive ladders 532 and 534 (respectively), have been described above. RF power supply 510 drives the primary of transformer 520, with one side of the secondary winding (center tap) energizing one of the electrode ladder and the other secondary winding energizing the other electrode ladder. In FIG. 5a, the DC bias to electrode ladders 220a and 220b described in FIG. 2 are provided by resistors 518a and 518b, respectively, while the RF energization of those same ladders is provided through capacitive ladders 514a and 514b.

FIG. 5b shows a different approach, where the capacitive ladders 514a and 514b described in FIG. 5a are replaced by an arrangement with capacitors in parallel. Capacitors 524a provide the RF energization of electrode ladder 220a, while capacitors 524b provide the RF energization of electrode ladder 220b.

It is important that the same phase be connected to the same electrode ladder, either in the case of capacitive or inductive drive. This is clearly shown in the case of the capacitive drive circuits shown in FIGS. 5a and 5b, not clear in the case of the inductive drive shown in FIG. 3.

Also, although the circuits shown in FIGS. 3-7 are intended to use a driver using an oscillator, it is possible to use resonance to establish the RF electric fields, achieving the high voltage by operating at resonance from a low power/field power supply. Resonant circuits at low frequencies, as required for the circuits shown in FIGS. 3, 4, 5, 6 and 7 can be implemented by using discrete components. The phase shift elements required for operation with multiple waveforms that have been phase shifted can also be implemented using discrete components.

Figure 6A:
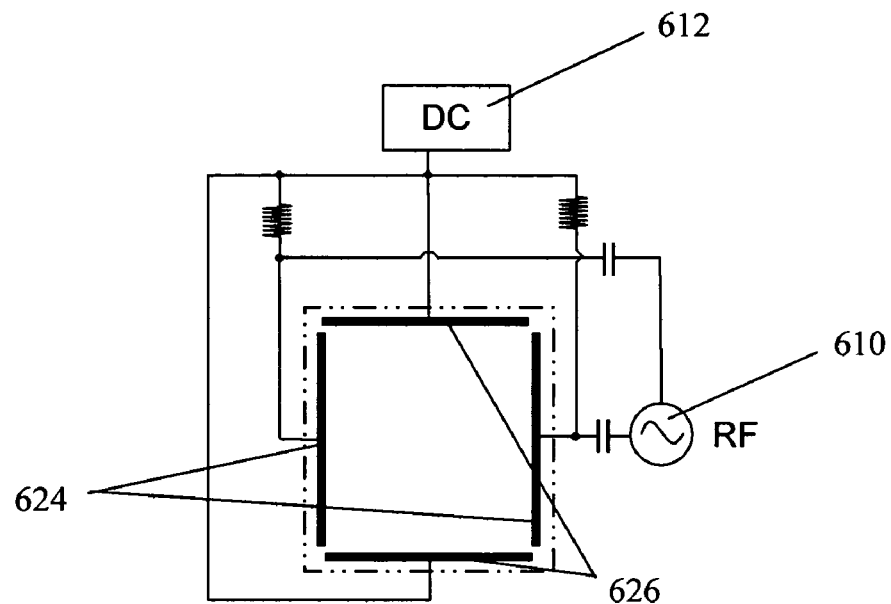
FIGS. 6a and 6b shows the cross sectional view of an embodiment of this device with a segmented guard electrode that is made from 4 segments.
Figure 6B:
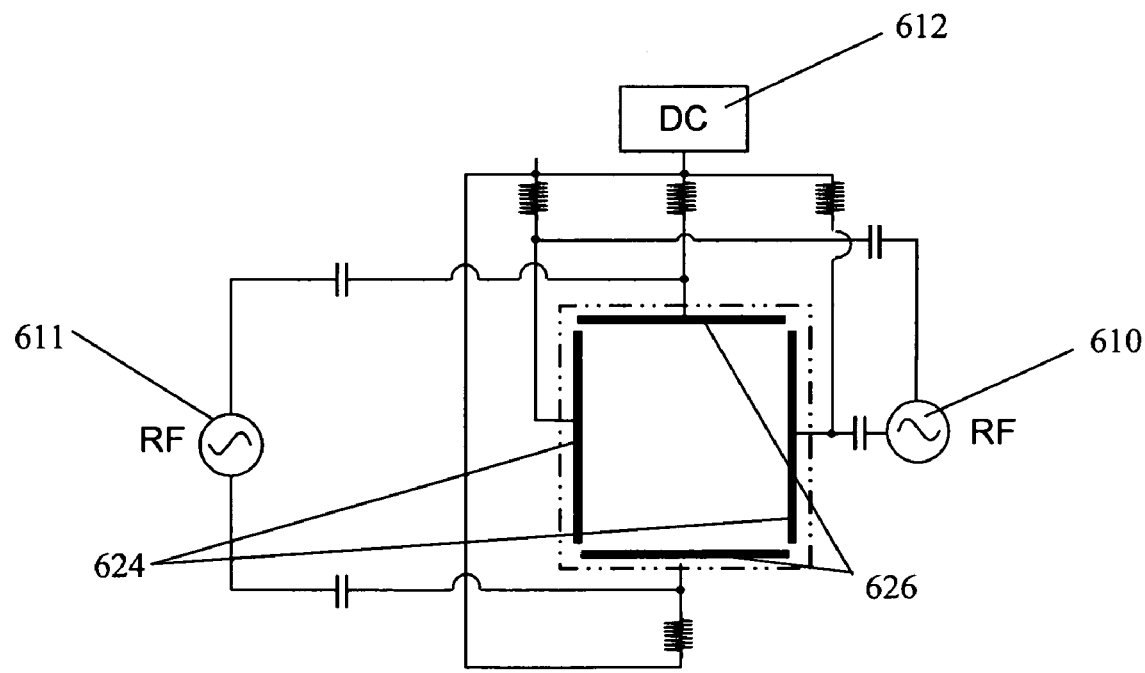

FIGS. 6a-6b show potential arrangement of the segmented guard electrodes. In the case of FIG. 6a, instead of circular or semicircular rings, the segmented guard electrodes are placed on a square (or rectangular) arrangement. The DC bias is provided by element 612 (from the DC ladder). RF power supply 610 energizes the segmented guard electrodes 624 with opposite AC polarities, while the segmented guard electrodes 626 are not energized by any RF. The electric field generated by the arrangement is approximately an electric dipole.

In FIG. 6b, two sets of RF sources are used in order to energized with RF voltages all the segmented guard electrodes. Coupled guard electrodes 624 are energized by RF power supply 610, while coupled guard electrodes 626 are energized by RF power supply 611.

Figures 7A, 7B:
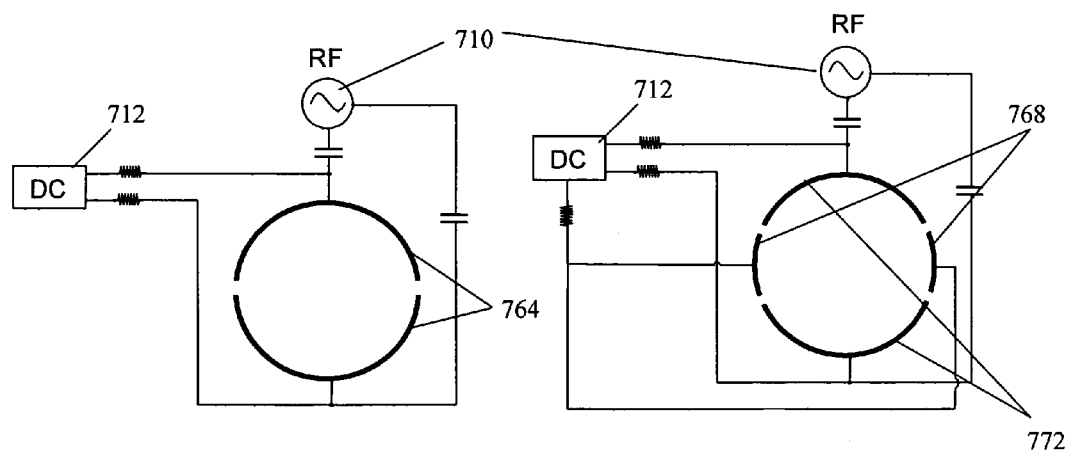
FIGS. 7a-d shows four cross sectional views of embodiments of this device with different arrangements for the segments that make the segmented guard electrodes.
Figures 7C, 7D:
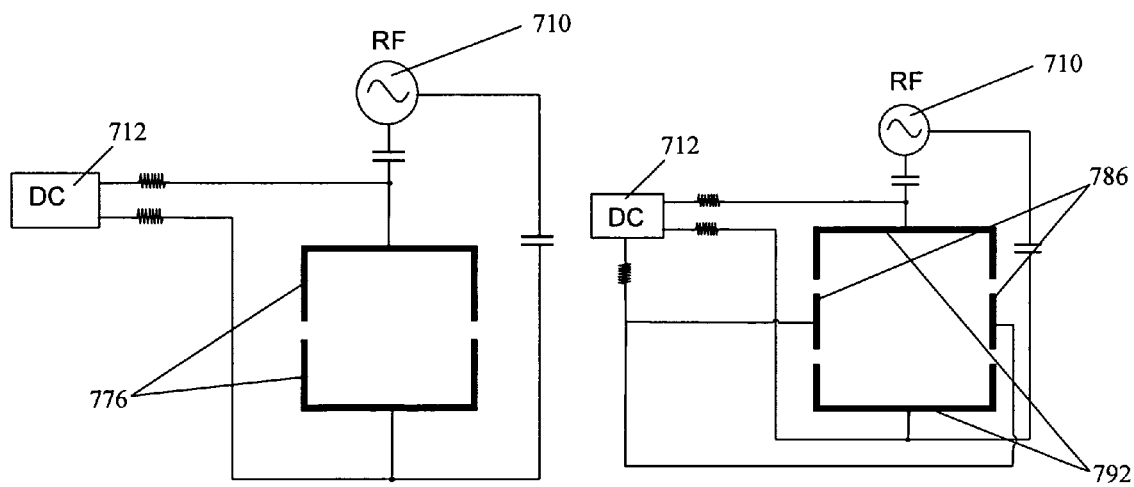

FIGS. 7a-7d show non-limiting configurations of the segmented guard electrodes that can also be utilized. For example the DC-biased segmented guard electrodes can be arranged in a circular, Cartesian-square, rectangular, or parallel plate pattern, but not not-limited to these. In FIG. 7a, the conventional circular electrode ring guards are split into two semicircular segmented guard electrodes, energized with RF by power supply 710 and DC-biased by element 712 from a DC ladder. There is no need for the number of electrodes to be just one pair, and FIG. 7b shows a case with 2 pairs of segmented guard electrodes 772 and 768. In FIG. 7b, only one pair of segmented guard electrodes is energized with RF, similarly to the case of FIG. 6a. FIGS. 7c-7d show cases with rectangular pattern or Cartesian-square shaped segmented guard electrodes. FIG. 7c shows an alternative set of segmented guard electrodes 776 to those shown in FIG. 7a, and FIG. 7d shows an alternative set of segmented guard electrodes 792 and 786 to those shown in FIG. 7b. The segmented guard electrodes are used to apply RF electric field to the drift tube, the segments may be configured in a variety of patterns; as shown in FIG. 7, it does not need to be evenly divided.

A single generator can be used at a single frequency, or multiple generators with multiple frequencies can be used. An electrode can have a superposition of these waveforms, or as shown in FIG. 6b different electrodes are operated with waveforms with difference frequencies.

At the higher frequencies of a few hundred MHz all the way up to 2.45 GHz resonant coupling is also possible though the establishment of resonant modes in a cavity. Especially attractive are applications at 750 MHz, 900 MHz, 1.8 GHz and 2.45 GHz, where inexpensive, very compact, efficient solid state drivers are available.

In some embodiments, the method for separating ions comprises: introducing ions into an ion mobility based spectrometer, transporting and/or separating ions while supplying energy to the ions maintaining them at an energy level that is higher than the thermal energy at a given operating temperature, and preventing ions from continuously staying at the thermal energy level for substantially greater than 1 µs throughout the transportation and/or separation process. The energy is provided by a RF electric field that's magnitude is relatively constant in time by generating an RF field that rotates as a result of superposition of fields generated by different electrodes and RF drivers. In addition, the RF drivers operate at the same frequency but different phases.

There are multiple means to generate the symmetric RF fields. Some of the potential geometries are shown in FIGS. 6a-6b and 7a-7d. FIG. 7a shows the electric configuration of the time of flight ion mobility spectrometer where the electrodes are used as guard electrodes as well as the oscillator providing an RF electric field with a given waveform. The RF electric field is substantially perpendicular to the DC electric field for ion separation. In FIGS. 6a-6b and 7a-7d the RF fields is substantially normal to the DC field.

Figure 8:
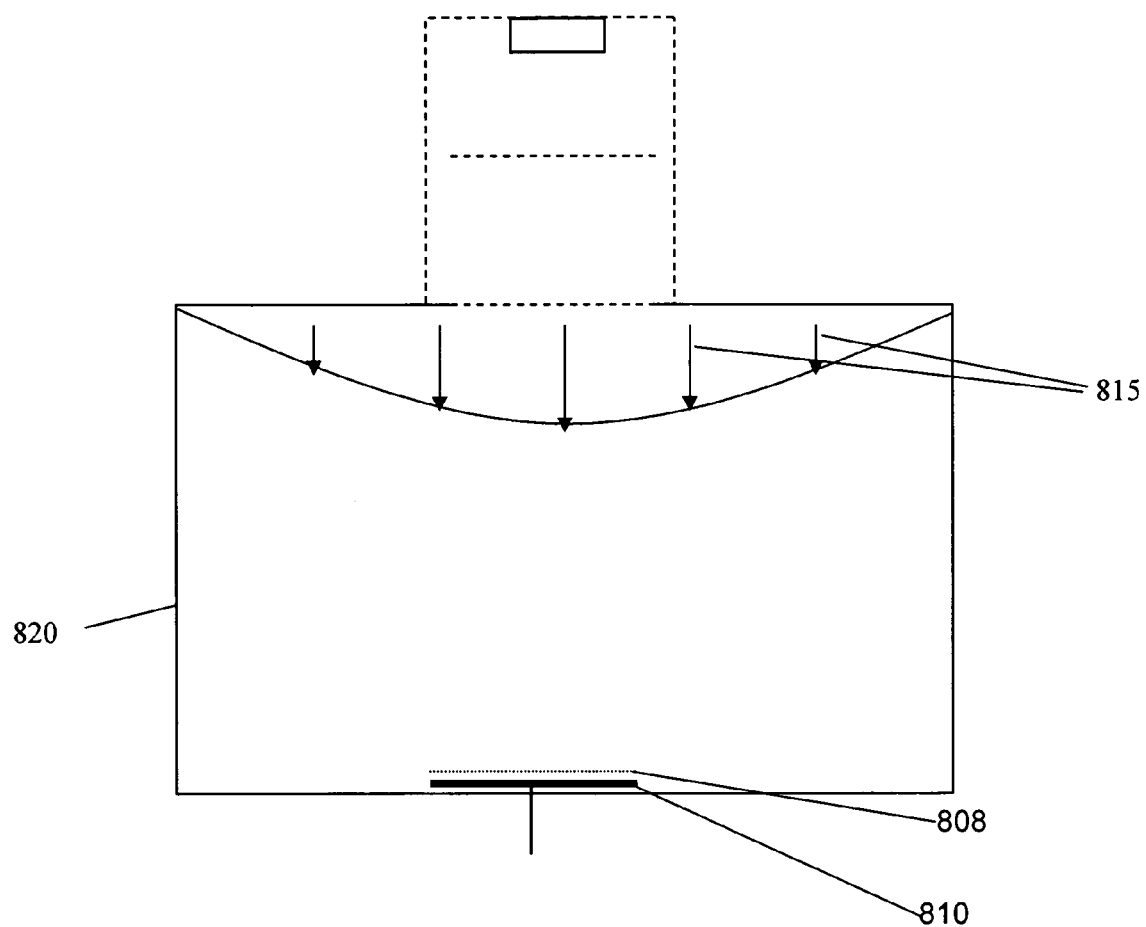
FIG. 8 illustrates the use of high frequency cavity modes to establish the RF field of the present invention.

In another non-limiting example, the RF electric field is substantially parallel to the DC field, with a RF field generated by a resonant cavity. FIG. 8 shows an ion mobility spectrometer with a cavity that uses RF fields in the microwave range of frequencies. The collector aperture and the ion detector are located inside the RF cavity 820 in FIG. 8, but this is for illustration only and the ion aperture could be part of the RF cavity and the ion detector just outside the cavity. The cavity indicated shows an electric field structure 815 of the TM010 mode which results in axial electric fields, but this does not need to be the case and other mode can be used. FIG. 8 shows a schematic of a drift tube that is inside an RF cavity, illustrated as a TM010 cavity, which may also contain a collector aperture 808 and a ion detector 810. High frequencies can be used to generate high values of RF electric field, coupled through antennas or waveguides. RF power is decreased by use of high Q-cavities. In this case the RF electric field is constant in the axial direction, but decreases in the radial direction. Thus only the central region of the cavity is used for ion transit. Other modes can be used, as well as other cavity geometries. Fields higher than 500 MHz would be required in order to minimize the size of the cavity. For example, the frequency of the resonance could be between 500 MHz and 3 GHz. Inexpensive, efficient power supplies (magnetrons, solid state components) exist in this frequency range.

Figure 9:
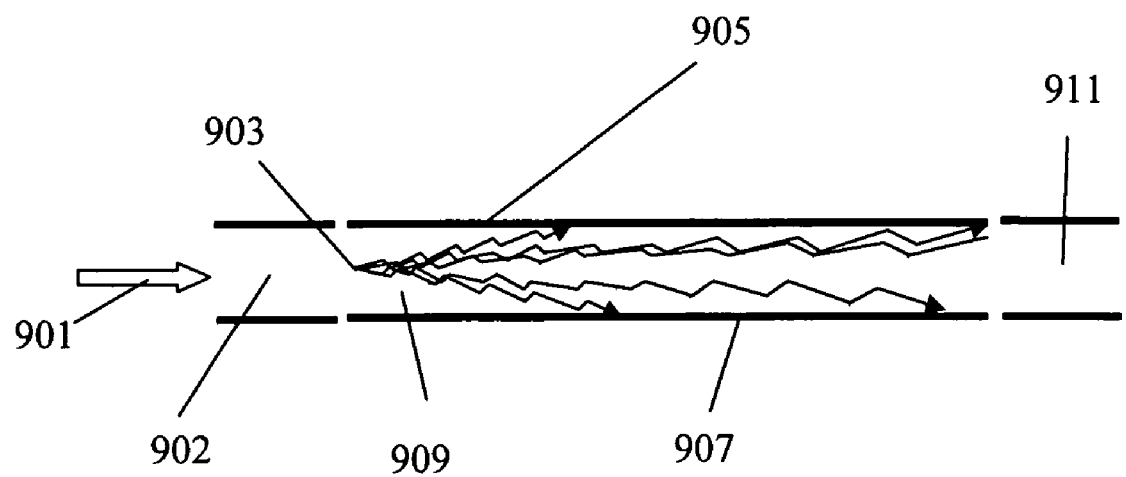
FIG. 9 shows the trajectories of ions in the gap between the upper and lower parallel plate electrodes of a FAIMS or DMS ion filter, under the simultaneous influence of the carrier gas flow and an asymmetric radio frequency electric field waveform.

The generally accepted method and apparatus for operating a FAIMS or DMS device for ion filtering is shown in FIG. 9. A stream of carrier gas 901 transports ions 903 through ion introduction section 902, longitudinally down the drift tube (ion filtering section 909) between the gap between the upper 905 and lower 907 parallel plate electrodes of the ion filter, and then detected in the ion detection section 911. If an asymmetric RF electric field is then applied to the electrodes the ions will oscillate in a perpendicular direction to the carrier gas flow, in response to the RF electric field, while moving down the drift tube with the carrier gas. During the simultaneous influence of the carrier gas flow and an asymmetric RF electric field waveform. A simplified asymmetric RF electric field waveform is shown in FIG. 10a.

Figure 10A:
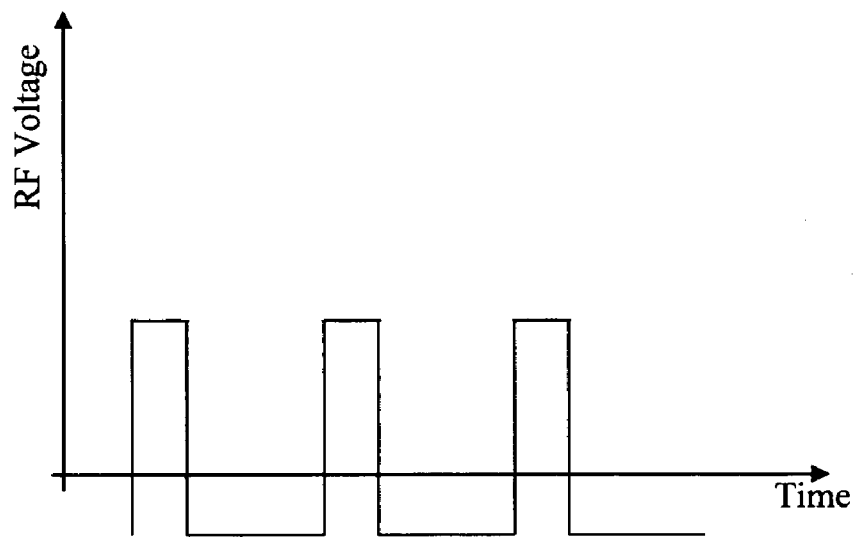
Figure 10B:
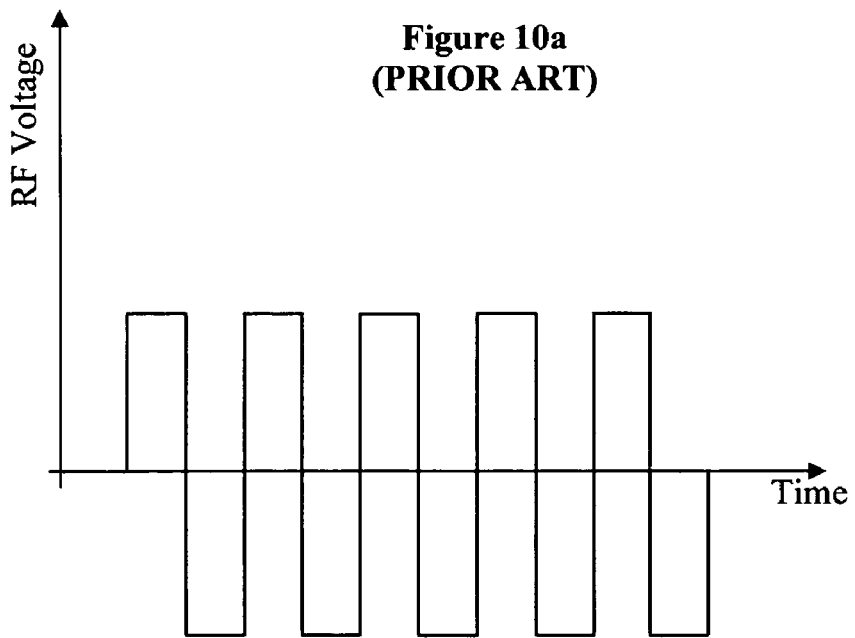

FIGS. 10a-10d show different waveforms. FIG. 10a shows the waveform of the conventional FAIMS or DMS devices that consists basically of an asymmetric AC field with a variable DC bias. The present invention uses symmetric AC fields, as shown in FIG. 10b, which shows square waves, but could use other types of waveforms, such as sinusoidal waveforms. A big advantage of using symmetric sinusoidal waveforms is that resonant circuits can be used to generate the RF, simplifying substantially the power supplies. FIG. 10c shows another embodiment of the application. It is not necessary to use the same frequency in all the electrodes. Multiple RF power supplies, as shown in FIG. 6b can be used, operating at difference frequencies. Alternatively, in the differential mobility spectrometer the waveform can be a superposition of symmetric and asymmetric waveforms, as shown in FIG. 10d. In this non-limiting example, the high frequency waveform is used to supply energy and the low frequency asymmetric field is used to cause ion mobility based separation.

Figure 11:
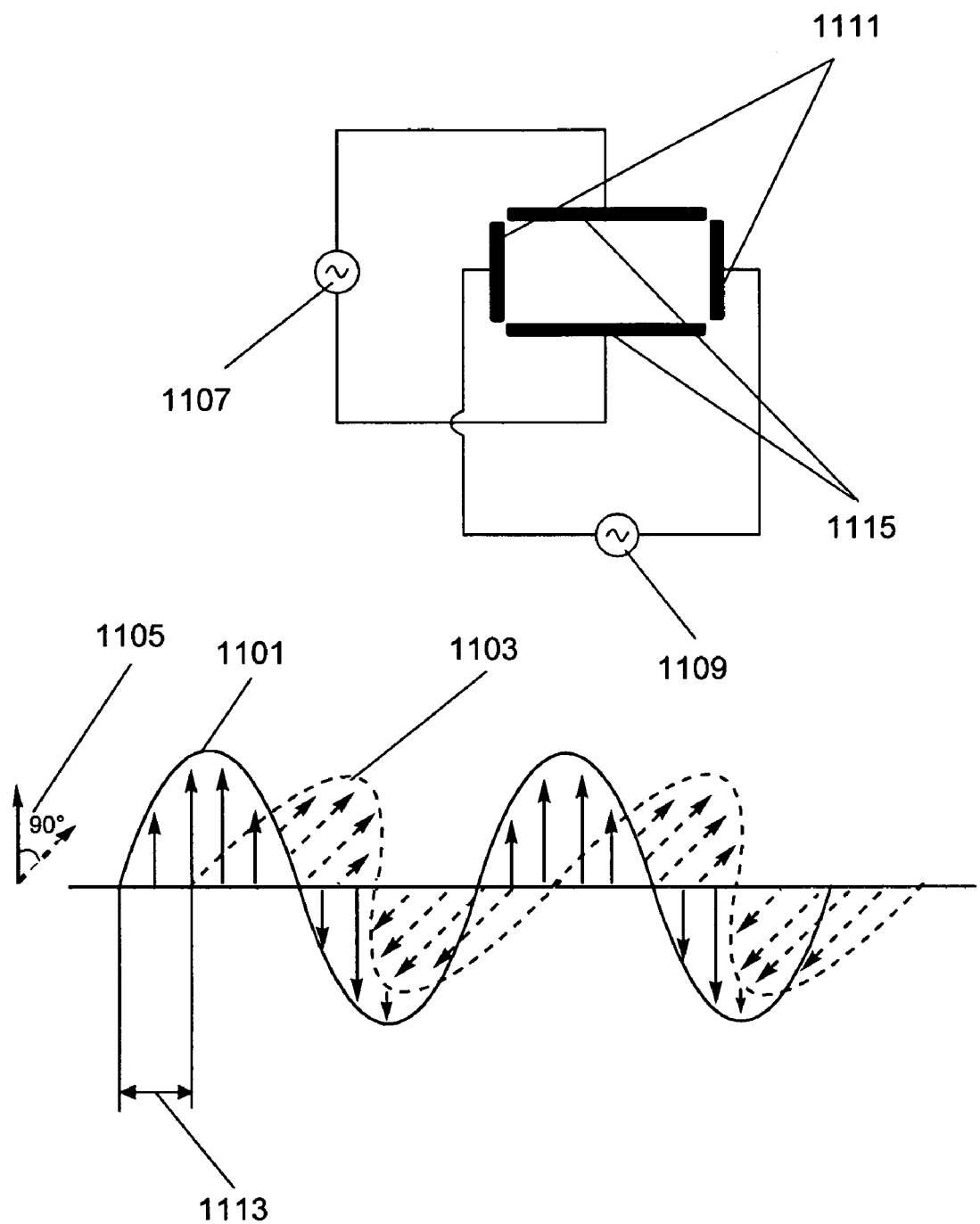
FIG. 11 shows one embodiment of the waveforms used for EE-IMS, where the an RF electric field is applied in the direction that is perpendicular to the direction of another RF electric field with an substantial phase offset.

In FAIMS or DMS, the field is high in one fraction of the cycle but low on the rest of the cycle. The clustering phenomena can affect the ion during the low field period, and authors have commented that it is this process that allows for ion separation in these devices. In contrast with FAIMS or DMS devices, in one embodiment of the present invention, the RF field should be high on all of the cycle to prevent the clustering. These RF fields are used to set the ions at certain energy level, in practical applications to minimize the clustering of the ions. The RF fields can be in the same direction as the asymmetric electric fields, or they can be in the direction normal to them. As such, FIG. 11 can apply an asymmetric electric field to source 1107 for FAIMS based separation and a symmetric RF field to source 1109 for energy elevation. FIG. 11 shows two waveforms 1101 and 1103 that could be supplied to the RF field source 1107 and 1109, respectively. In this non-limiting example, ions inside the device experience a RF electric field resulting from waveform 1101 and 1103 as there are applied to electrodes 1111 and 1115 respectively. It is also shown in the figure the two waveforms oscillate in directions that are normal (90 degree) 1105 to each other. The example also shows the two waveforms have a phase offset 1113. In case of applying this waveform configuration to a FAIMS device, one of the waveforms (e.g. 1101) could be asymmetric as required to achieve separation (in this case, electrodes 1111 is used as the parallel plates in prior art DMS) and the other waveform (e.g. 1103) can be symmetric for supplying energy to the ions.

Figures 12A, 12B:
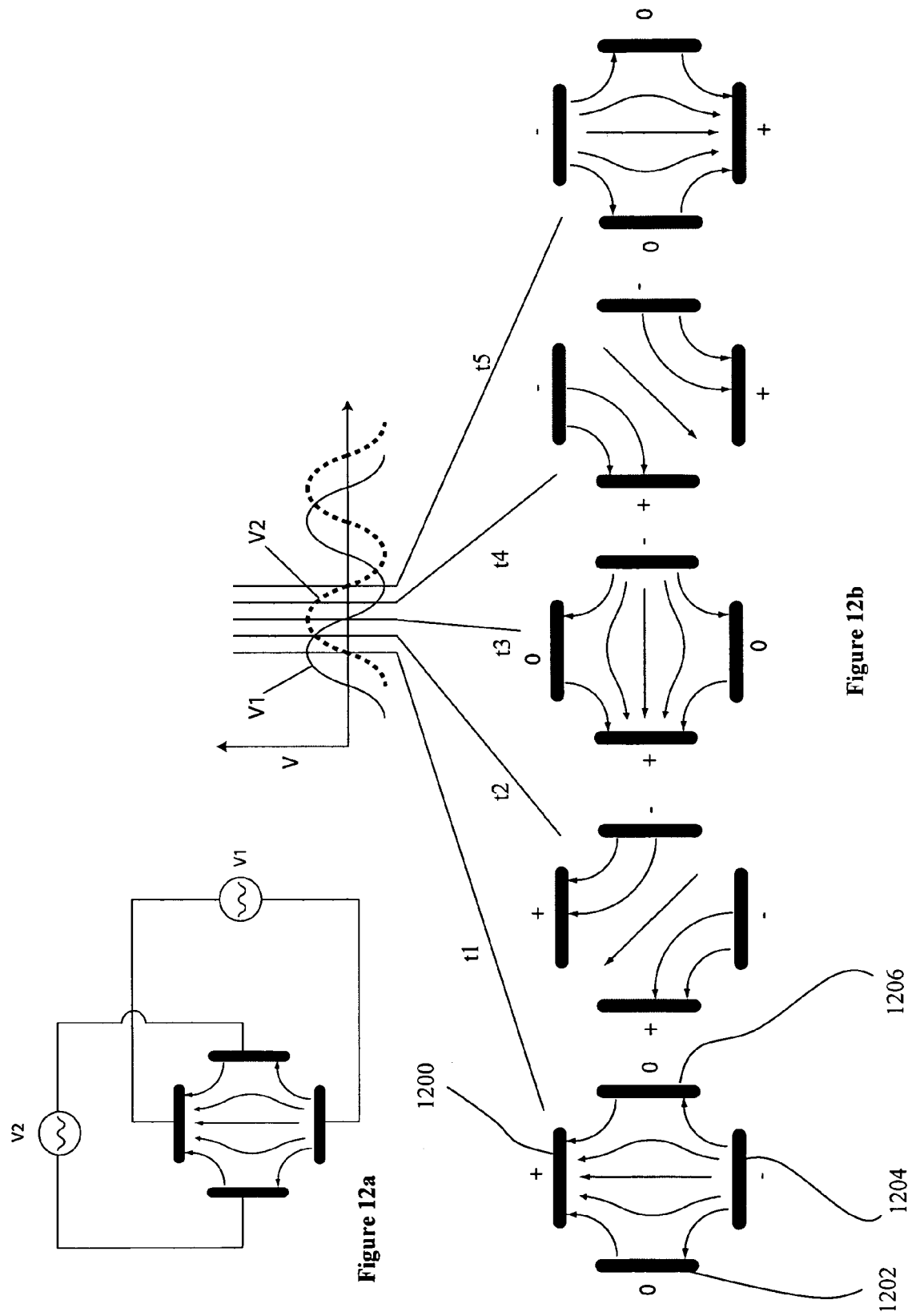
FIGS. 12a-12b shows means of generating rotating RF electric fields using 2 pairs of electrodes.

In another set of embodiments, the energy is supplied continuously during ion transportation and/or mobility based separation process, such that the energy of the ions is always above the thermal energy level. If linear electric fields are provided, the RF ion motion is along the RF field direction, and the ions at the end of the oscillatory motion lose their additional energy (twice in a cycle, at each end of the oscillatory path) and become thermal, where clustering could begin. The ions can be maintained at elevated energy by using superposition of electric fields. FIG. 12a-12b shows an embodiment with two sets of electrodes that generate electric fields that are in different directions. By energizing them using RF waveforms that have a phase difference (90 degrees in the case of FIG. 12a-12b), it is possible to obtain an electric field whose magnitude is relatively constant but is changing orientation (analogous to linear vs circular polarization of electromagnetic waves). The ion motion is in general an ellipse (not a line), and if the RF voltages and the electrode gaps are the same, the motion is a circle. Thus the ions are maintained at all times at high energy, and the RF electric field magnitude does not cross 0 at any time during the cycle. A large advantage of this embodiment is that lower frequencies can be used. In this embodiment, frequencies from 10's of kHz, can be used.

FIGS. 12a-12b show an embodiment where the RF electric fields are always on, without the short period that occurs when the RF electric field value goes through zero. FIG. 12a shows two sources with different waveforms V1 and V2. A single power supply generates the voltage, but the signal is split, with each leg carrying a different delay. FIG. 12b shows the case when V2 is phase delayed by 90 degrees. The RF electric field structure is illustrated during half-cycle of the waveform. At time t1, the RF electric field structure is such that the field is vertical, with the top electrode 1200 having the highest RF voltage (electrode 1204 having the lowest RF voltage) and electrodes 1202 and 1206 not having any RF voltage. Time t2 (45 degrees later) shows the conditions when the RF voltage of electrode 1200 is lower and the same of electrode 1202, with electrodes 1204 and 1206 with opposite polarity. The RF electric field has rotated 45 degrees. At time t3, electrode 1202 has the highest RF voltage and the field has rotated 90 degrees. The field at 135 and 180 degrees is subsequently shown in FIG. 12b. It should be noted that the ions experience not a linear oscillatory motion in this field, but they move in circles. If the amplitude of voltages V1 and V2 are not the same, or the gaps between coupled electrodes 1200, 1204 and electrodes 1202, 1206 are not the same, the ions move in elliptical motion. FIG. 12b shows that it is not necessary for the RF field to cross 0 value, where the lack of energy of the ions could alter the clustering properties of the ions. The choice of the phase delay determines the direction of rotation of the RF electric field. With V2 delayed with respect to V1, the RF field rotates in the counterclockwise direction. If V2 is delayed with respect to V1, the RF field would rotate in the clockwise direction.

An alternative embodiment, the configuration described in FIG. 11 can be used as one set of the guard electrodes for TOFIMS. In this case, both waveforms could be symmetric. With the phase offset 1113 between these two RF waveforms, the ions will be continuously maintained at elevated energy level during the process of ion transportation and separation in the spectrometer.

In some embodiments, the method for separating ions may comprise the introduction ions into an ion mobility based spectrometer followed by the transportation and/or separation of ions while supplying energy to the ions maintaining them at an energy level that is higher than the thermal energy at a given operating temperature. Examples are described in embodiments shown in FIGS. 11 and 12. The ions can continuously stay at the elevated level throughout the ionization, reaction, separation, and/or other transportation processed in ion mobility spectrometers.

It should be stressed that it is advantageous for the innovation for the RF field to be relatively uniform through the space where the ions move, so that all ions have the same properties. Thus the electric field is dipole like, as shown in FIG. 12*b*, NOT quadrupole like, which can be used for either focusing or selecting ions.

In FAIMS or DMS devices, the high RF electric fields are present only in the separation region. In the novel EE-IMS, the high RF electric fields is also present in the ionization chamber and/or the reaction region in order to prepare the ions at a given energy level before entering the separation region, in one embodiment, the energy level can be substantially similar to the energy level supplied to the separation region.

It is possible to modify the method of operation of differential mobility spectrometers to take advantage of the application of symmetric waveforms to obtain the advantages described in this application. It is possible to superimpose symmetric waveform with asymmetric ones. The ion chemistry and temperatures are adjusted by the symmetric waveform, while the separation is achieved through the asymmetric waveform. The direction of electric field of the symmetric RF field can be in the same direction as the direction of the asymmetric field, or they can be at normal directions. FIG. 6*b* shows a case in which the directions of the symmetric and asymmetric fields are mostly normal to each other. The applied waveform in the case that the waveforms are applied to the same set of electrodes is shown in FIG. 10*d*. Symmetric waveforms are superimposed on top of asymmetric waveforms. There can be applied DC bias on the final voltage applied to the electrodes.

Because the drift tube does not have to be miniaturized, as in the case of the DMS devices, lower frequencies can be used. In those devices, frequencies need to be high to minimize the ion drift during the half cycle that the ions are drifting in one direction prior to reversing direction. The lower frequencies used in the sensor heads simplify the electronics, requiring lower price components and also decreasing losses in ferrite-based transformers. RF fields on the order of 5-15 kV/cm will be required, operating at frequencies on the order of 100-500 kHz. The relatively large size of the instrument allows frequencies as low as a few 10's of kHz. Relatively simple waveforms are required (either sinusoidal or square wave), easily generated using conventional MOSFET technology and amplified using efficient compact ferrites.

The schematic diagrams shown in FIGS. 1-7 operate in a mode in which the RF and DC electric fields are mostly normal. Particularly, the figures in the drawing section describe examples providing the AC field in the direction that is substantially perpendicular to the DC electric field. This does not have to be the case. It is possible to have geometries where the DC and RF fields are substantially aligned. There may be advantages to this configuration, especially for reduced size drift tubes. It is intended to include this mode of operation as a different proposed embodiment.

Figure 13:
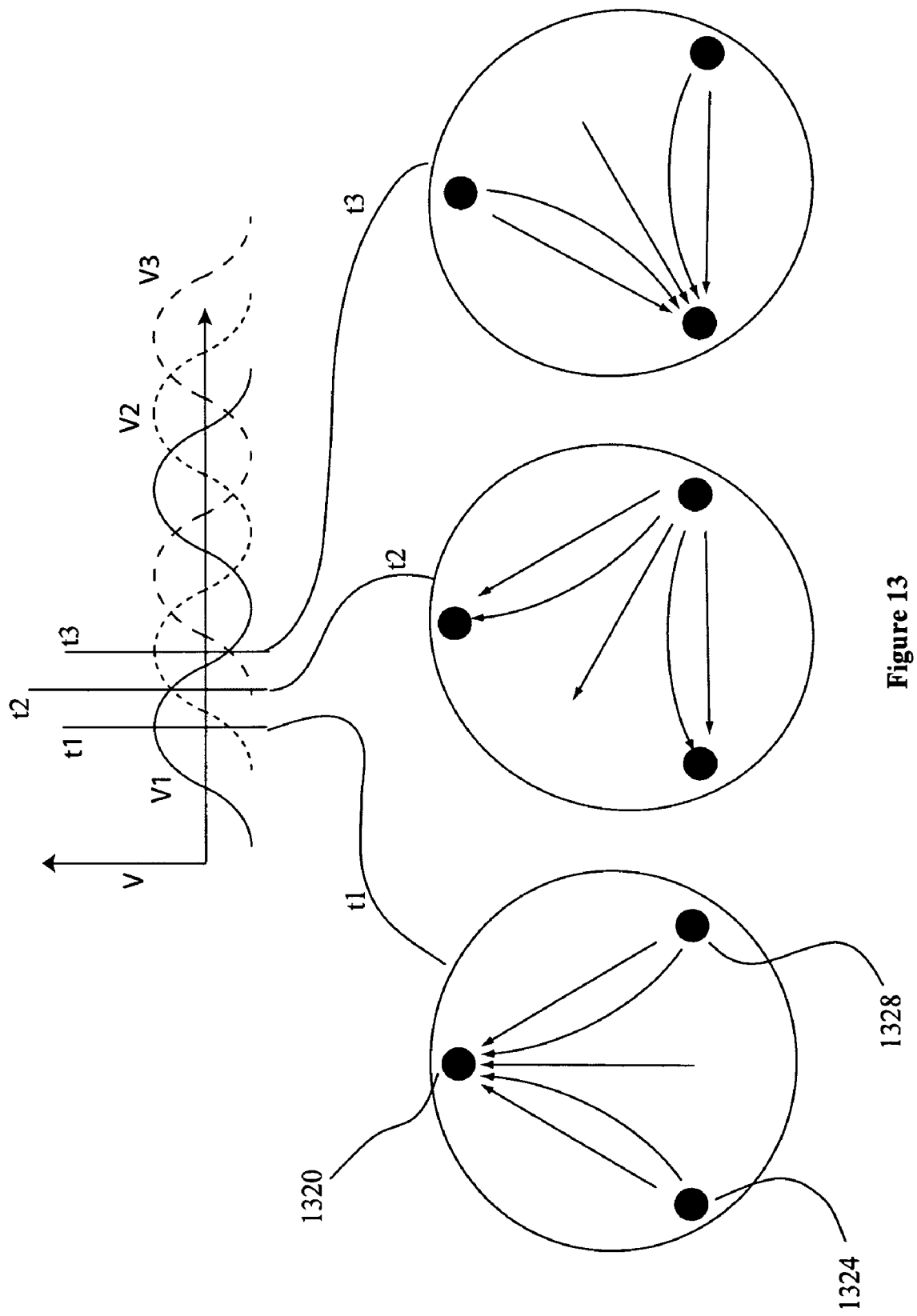
FIG. 13 shows means of generation rotating RF electric fields using an uneven set of electrodes.

To illustrate the nature of the RF electric field in this invention, FIG. 13 indicates that the electric field with an odd number of electrodes. Three electrodes are shown in FIG. 13. The figure is to illustrate the operating principle; the size and shape of the electrodes may be altered to generate desired electric field inside the drift tube as well as guard interferences from outside the drift tube. Each electrode is energized by a different waveform, V1, V2 or V3, which have been phase delayed with respect to each other. At time t1 electrode 1320 has the highest voltage, with electrodes 1324 and 1328 equal voltage of the opposite polarity. At time t2 (60 degrees later), electrodes 1320 and 1324 have the same polarity, with electrode 1328 having the lowest voltage, and the field direction and shape is changed. Finally, at time t3 (120 degrees later) electrode 1324 has the highest voltage, with electrodes 1320 and 1328 having opposite polarity voltages. The ions in this case move in near circular motion.

Figure 14:
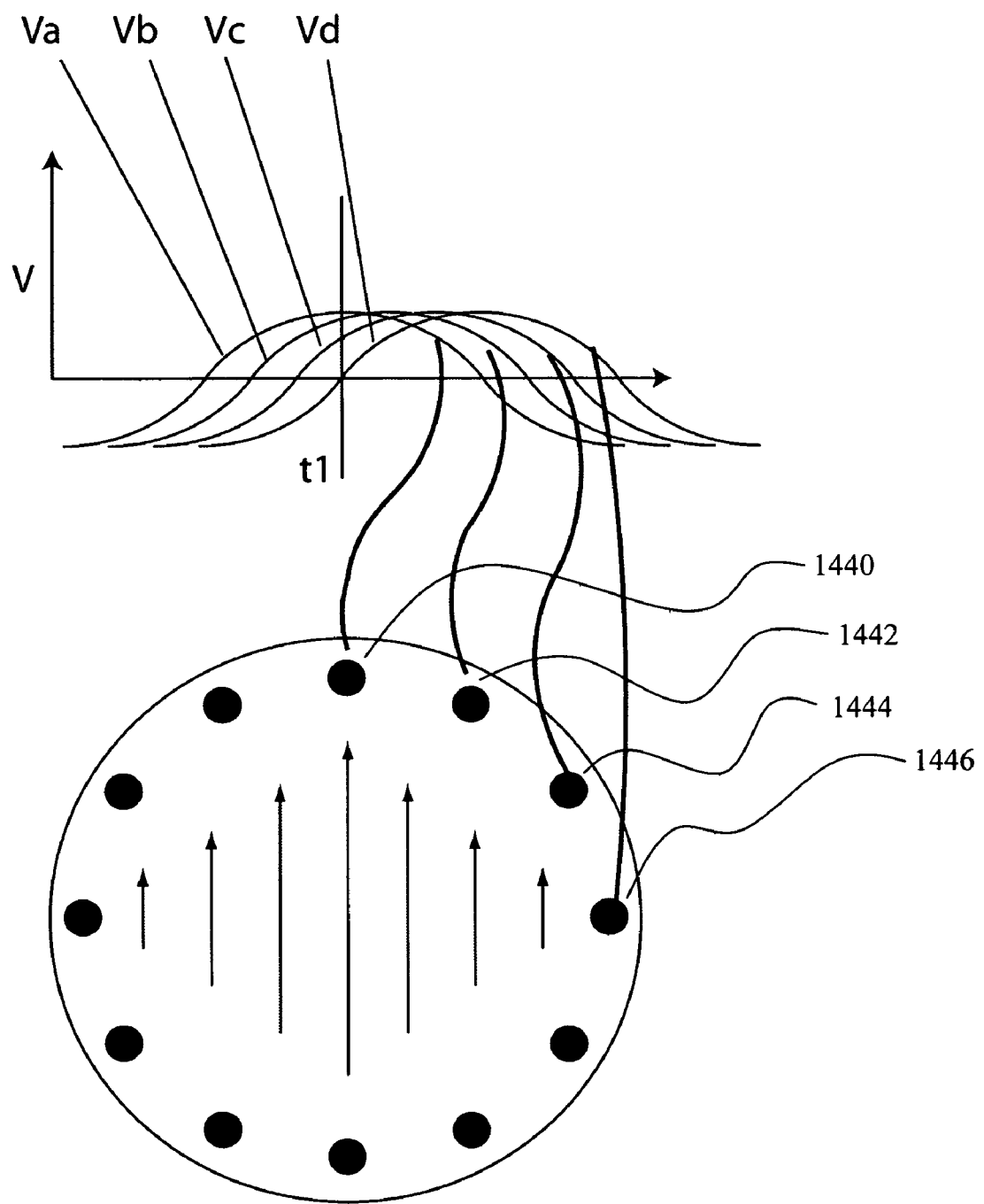
FIG. 14 shows means of generating a relatively uniform RF electric field in the EE-IMS using multiple electrodes.

The preferred RF electric field is relatively uniform over the volume where the ions travel. In this manner, the non-thermal energy of the ions on a cross section of the device is uniform. Thus, concepts that use non-uniform fields, such as quadrupole fields, are not of interest to the present application. Those fields are used in other concepts for focusing the ions. Uniform RF electric fields can be generated using a larger number of segmented guard electrode that are driven by different waveforms. FIG. 14 shows one with 12 electrodes, driven by phase-shifted electrical waveform generated by one source. It is possible to also use multiple sources. There is no need for an even number of electrodes, and FIG. 13 shows a concept using an odd number of electrodes.

Figure 15:
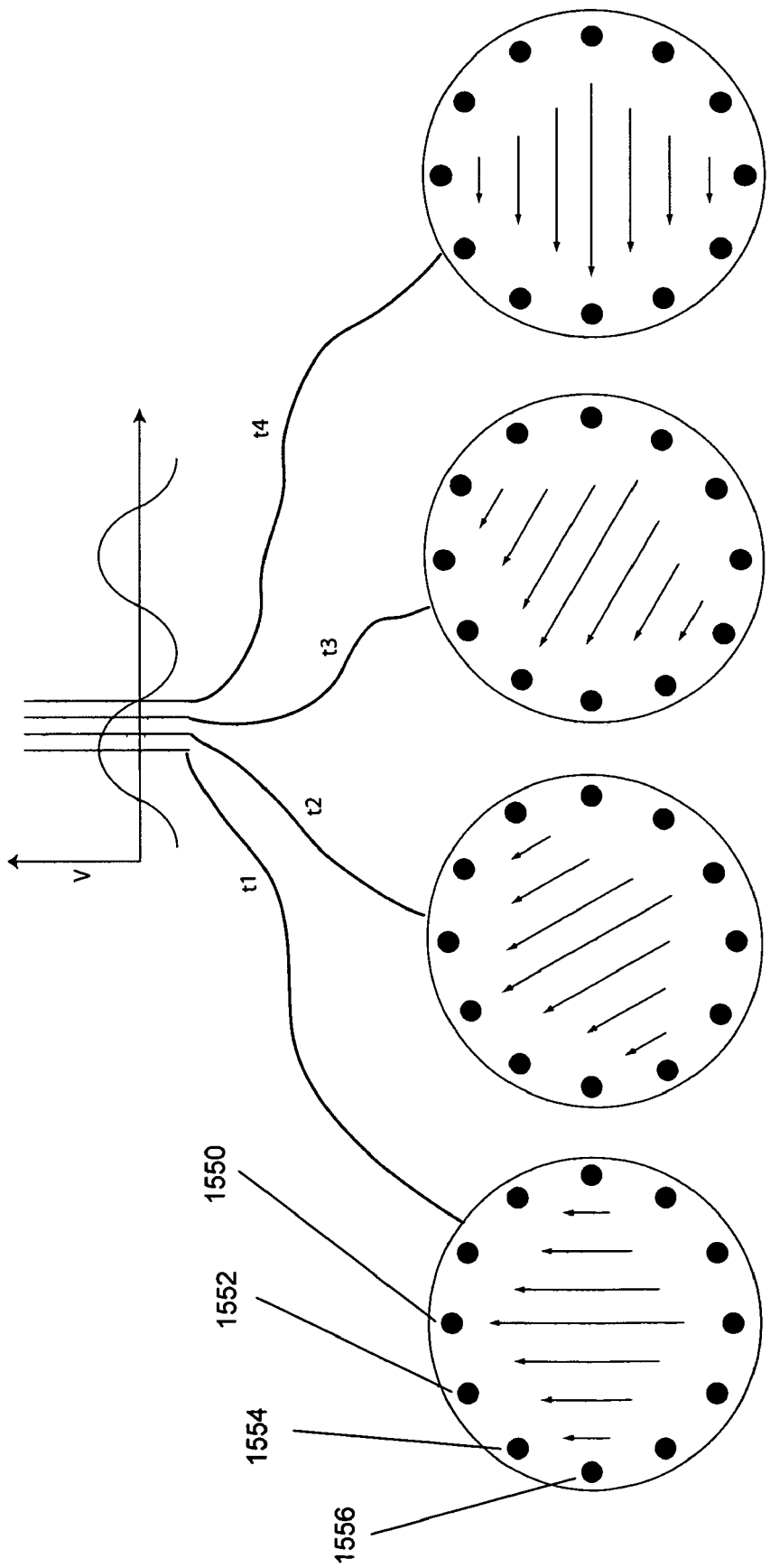
FIG. 15 shows means of generating rotating, relatively uniform RF electric fields in the EE-IMS using multiple electrodes and multiple waveforms.

FIG. 14 shows means to generate nearly uniform electric fields. Multiple sets of segmented guard electrodes (12 in the case of FIG. 14) are located around the peripheri of the ion mobility spectrometer. As in the case of FIG. 13, the electrodes are energized by a RF waveform that different delays for different electrodes. Only 4 waveforms are shown in FIG. 14, Va, Vb, Vc and Vd for energizing electrodes 1440, 1442, 1444 and 1446, respectively. By appropriately choosing the phase delays it is possible to generate nearly uniform RF fields within the space of the ion mobility spectrometer. In the case illustrated in FIG. 14, the different electrodes have been delayed with respect to the one nearest counterclockwise, by 30 degrees. At time t1 shown in FIGS. 14 and 15, electrode 1440 and 1550 has the highest voltage, and the field orientation is vertical, with relatively uniform fields pointing in the direction of electrode 1440 in FIG. 14 and 1550 in FIG. 15. FIG. 15 shows the time evolution of the electric field. Only the RF voltage applied to electrode 1550 is shown. At time t2 (30 degrees after time), RF voltage in electrode 1550 has decreased, but electrode 1552 has the highest RF voltage. The relatively uniform field rotates counterclockwise pointing in the radial direction towards electrode 1552. Similarly at times t3 and t4 the electric field points in the radial direction towards electrodes 1554 and 1556, respectively.

Figure 16:
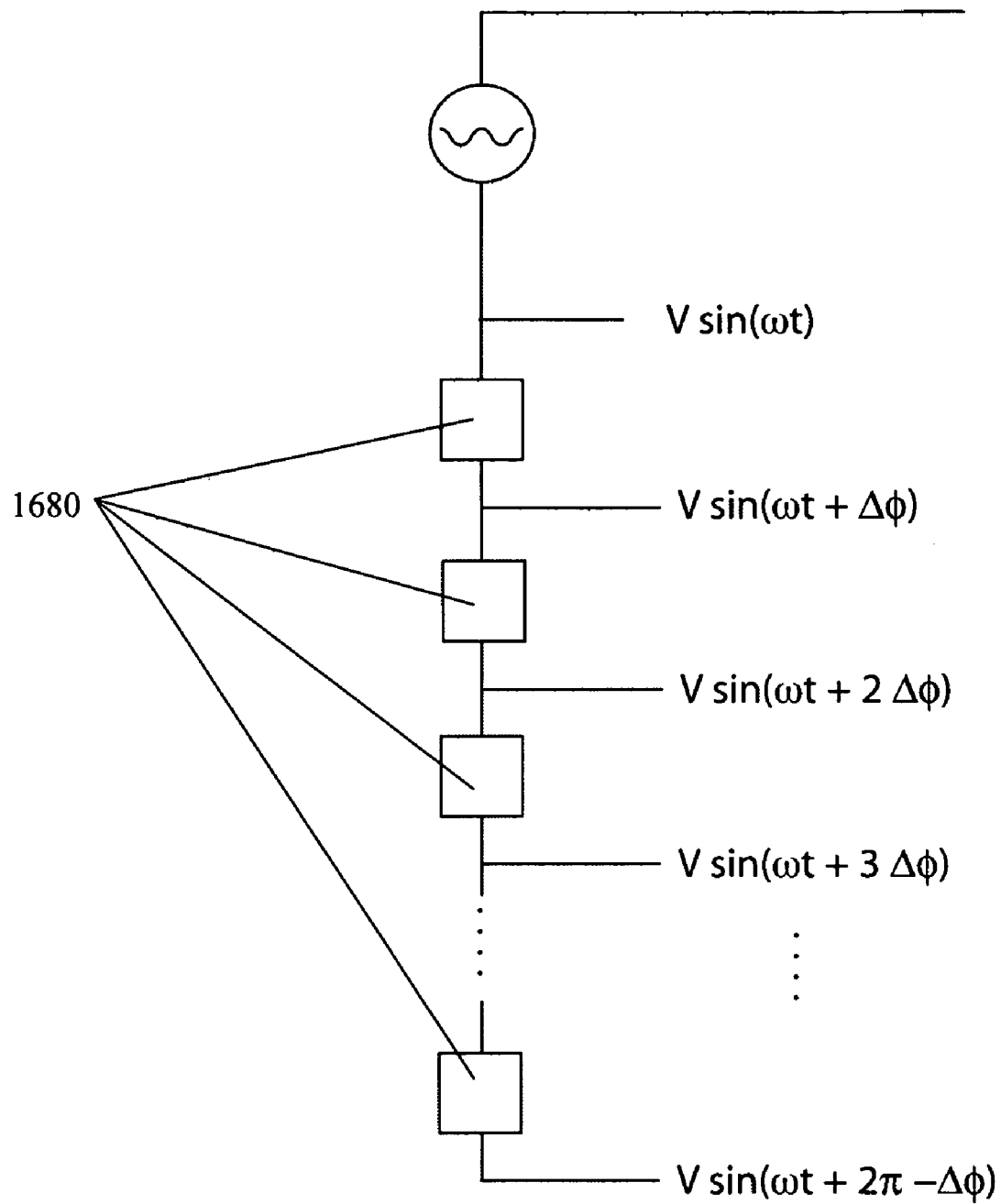
FIG. 16 shows means of generating multiple waveforms using phase delay elements that add a constant delay.
Figure 17:
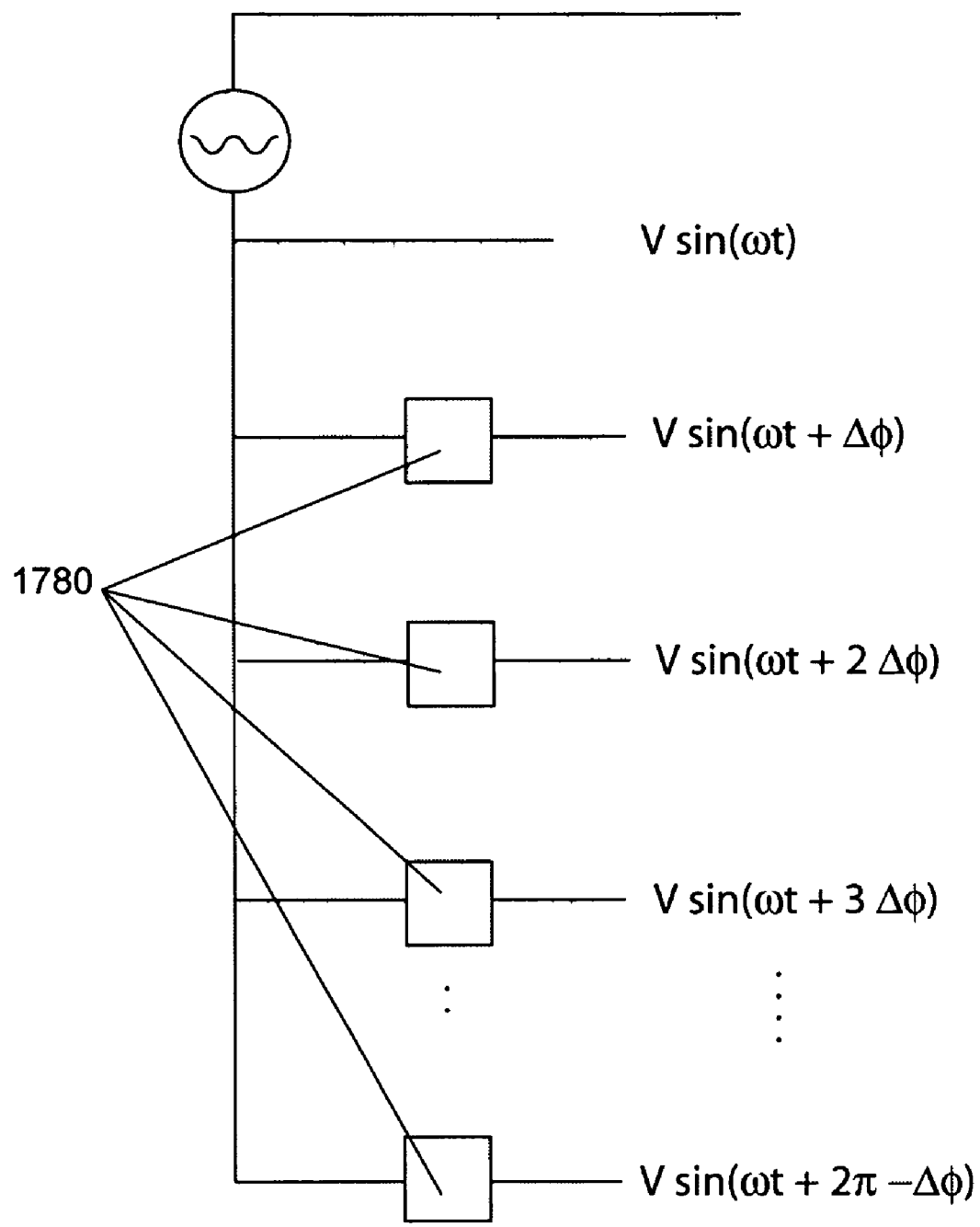
FIG. 17 shows means of generating multiple waveforms using phase delay elements that add multiple frequency delays.

FIGS. 16 and 17 indicate means of obtaining the multiple single frequency RF waveforms from a single source, through the use of phase delay elements. In FIG. 16, there are multiple phase delay elements 1680. The phase delay elements are in series, and the phase delays add up, generating a number of waveforms with multiple delays. In FIG. 17, the signals and the phase delay elements 1780 are in parallel. Each phase delay element provides a different delay.

The kinetic energy of ions in the EE-IMS is controlled by adjusting the amplitude of the RF component of the electric field. Multiple frequency and amplitude can be select for different energy level, or effective temperature, of ions. The method of sweeping through a frequency or amplitude range during the analysis of a sample mixture can be used to identify ions that with different ion-molecular association energy levels. Ions with the same steady state mobility can be distinguished using their difference in association/dissociation energy.

The ion mobility spectrometer and the method of elevating energy of charged particles while traveling in an electric field can also are used to enhance the desolvation process for electrospray ionization process, wherein the electrosprayed ions are formed in a desolation region that is in front of the drift region in a ion mobility drift tube to replace the reaction region of IMS with other kind of ionization source. For a FAIMS system, the desolvation region is arranged in front of the ion analyzer.

The waveform of the RF field in the EE-IMS is not very important, as long as it is high enough on both polarities. It is best if the RF field is symmetric. It is also preferred if the RF field is substantially square-wave, in order to minimize the time during the electric field reversal between half-periods, although sinusoidal waveforms are much easier to generate using resonant circuits. The time for chemistry is thought to be about microseconds, thus the time during the 0-V RF field cross over should be on this time scale. Either high frequencies, over 100 kHz, or square waves at lower frequencies, would be desirable.

As shown in FIG. 5a, energy level added in the reaction region and drift region can be significantly different by using different waveform of the AC electric field components. The waveform can be in a broad range of RF waveforms, it could be in a range from 10 KHz to 10 GHz, particularly, in 1-10 MHz, particularly in several hundreds MHz to several GHz range, in particular the RF electric field frequency is between 10 kHz and 2 MHz, in particular the RF electric field is between 500 MHz and 3 GHz. In general, the RF field can be in a direction that is between substantially parallel to anti-parallel to the DC electric field as long as the ions stay at high energy level, i.e. time of ions stay at low energy level is significantly short and there is no cluster could be formed during this period of time. Particularly, the figures in the drawing section describe examples providing the AC field in the direction that is perpendicular to the DC electric field.

In a variety of embodiments, the EE-IMS can be developed into a true Compact Detection System. Compared to deployed IMS detectors, the EE-IMS based system provides better sensitivity and resolution by eliminating the use of a membrane inlet (that cause IMS sensitivity loss and memory effects) and drying materials (that increase instrument dimensions and consumable cost). It will also provide optimal spectrometer conditions for detection of both explosives and CWA simultaneously by eliminating cluster interference and operating temperature conflicts. The system can have advanced features, including: (a) IMS immune to moisture interference, (b) Low power consumption—no spectrometer heating necessary, (c) Simultaneous explosive particle and vapor detection, and (d) Improved IMS sensitivity. In alternative embodiments, the EE-IMS system can be constructed into a larger scale research grade system. Thus a system will provide the tools to study gas phase ion chemistry in the ionization chamber (region), reaction region and/or drift region of ion mobility spectrometers. The drift tubes can be manufactured by metallizing the inner region of a dielectric tube. The pattern required for the electrodes can be generated either during the metallization process or through machining/grinding after uniform metallization of the tube.

It is recognized that modifications and variations of the invention disclosed herein will be apparent to those of ordinary skill in the art and it is intended that all such modifications and variations be included with the scope of the appended claims.

What is claimed is:

1. A time of flight ion mobility spectrometer comprising:
   a) a DC electric field guiding ions traveling along an axial direction of a drift tube wherein the ions are separated based on their steady state ion mobility; and
   b) an energy source that continuously supplies energy to the ions maintaining the ions at an energy level that is above the thermal energy at an given operating temperature the ions staying at the elevated level during ion transportation and/or mobility based separation process.

2. The time of flight ion mobility spectrometer of claim 1, wherein the drift tube is separated into a reaction region and a drift region by an ion gate.

3. The time of flight ion mobility spectrometer of claim 1, wherein the energy source is supplied to the ions in an ionization region, a reaction region, and/or a drift region of the drift tube.

4. The time of flight ion mobility spectrometer of claim 1, wherein the energy level is sufficiently high to prevent ions from and/or alter the degree of ions clustering with surrounding neutral molecules.

5. The time of flight ion mobility spectrometer of claim 1, wherein the operating temperature is ambient temperature.

6. The time of flight ion mobility spectrometer of claim 1, wherein the energy source is a radio frequency (RF) electric field.

7. The time of flight ion mobility spectrometer of claim 6, wherein the RF electric field is symmetric.

8. The time of flight ion mobility spectrometer of claim 6 wherein the normalized RF electric field is greater than 2 Townsend.

9. The time of flight ion mobility spectrometer of claim 6 wherein the normalized RF electric field is greater than 40 Townsend.

10. The time of flight ion mobility spectrometer of claim 6, wherein the RF electric field frequency is between 10 kHz and 2 MHz.

11. The time of flight ion mobility spectrometer of claim 6, wherein the RF electric field is between 500 MHz and 3 GHz.

12. The time of flight ion mobility spectrometer of claim 6, wherein the RF electric fields are generated by applying the RF electric fields to a set of DC-biased segmented guard electrodes.

13. The time of flight ion mobility spectrometer of claim 12, wherein the DC-biased segmented guard electrodes are arranged in a circular pattern.

14. The time of flight ion mobility spectrometer of claim 12, wherein DC-biased segmented guard electrodes are arranged in a Cartesian—square pattern.

15. The time of flight ion mobility spectrometer of claim 12, wherein DC-biased segmented guard electrodes are arranged in a rectangular pattern.

16. The time of flight ion mobility spectrometer of claim 12, wherein DC-biased segmented guard electrodes are arranged as a pair of parallel plate pattern.

17. The time of flight ion mobility spectrometer of claim 6, wherein the RF electric fields are generated using inductive means, with a single magnetic core and a single primary but multiple secondary windings.

18. The time of flight ion mobility spectrometer of claim 6 wherein the RF electric fields are generated using multiple inductive cores, with primaries that are run in series.

19. The time of flight ion mobility spectrometer of claim 6, wherein the RF electric fields are generated using capacitive means.

20. The time of flight ion mobility spectrometer of claim 6, wherein the RF electric fields are from substantially parallel to anti-parallel to the DC field.

21. The time of flight ion mobility spectrometer of claim 6, wherein the RF electric fields are substantially normal to the DC field.

22. The time of flight ion mobility spectrometer of claim 6 wherein the RF electric fields magnitude that is relatively constant in time by generating an RF electric field that rotates as a result of superposition of fields generated by different electrodes and RF drivers.

23. The time of flight ion mobility spectrometer of claim 22 wherein the RF drivers operate at the same frequency but with different phases.

24. The time of flight ion mobility spectrometer of claim 22 wherein the RF electric fields operate at different frequencies from different sources.

25. The time of flight ion mobility spectrometer of claim 6 wherein the RF electric fields are substantially uniform in space by the use of multiple segmented guard electrodes driven with waveforms that have been phase shifted with respect to one another.

26. The time of flight ion mobility spectrometer of claim 6, wherein the RF electric fields are generated by using the drift tube as a resonant cavity, the frequency of the resonance between 500 MHz and 3 GHz.

27. The time of flight ion mobility spectrometer of claim 6, wherein the RF electric fields are generated by placing the drift tube inside a resonant cavity, the frequency of the resonance between 500 MHz and 3 GHz.

28. A time of flight ion mobility spectrometer comprising:
   a) a DC electric field guiding ions traveling along an axial direction of a drift tube wherein the ions are separated based on their steady state ion mobility; and
   b) an energy source that supplies energy to the ions maintaining them at a energy level that is higher than the thermal energy at an given operating temperature and preventing ions from continuously staying at the thermal energy level for substantially greater than 1 µs throughout the ion transportation and/or separation process.

29. An field asymmetric ion mobility spectrometer comprising:
   a) a introduction section that receive ions from an ion source, an ion filtering section that separate ions, and an ion detection section; and
   b) an energy source that supplies energy to the ions maintaining them at a energy level that is higher than the thermal energy at an given operating temperature and preventing ions from continuously staying at the thermal energy level for substantially greater than 1 µs throughout the ion transportation and/or separation process.

30. The field asymmetric ion mobility spectrometer of claim 29, wherein the energy source is a RF electric field.

31. The field asymmetric ion mobility spectrometer of claim 30, wherein the RF electric field is symmetric waveform that is superimposed on the asymmetric waveform with a greater frequency.

32. The field asymmetric ion mobility spectrometer of claim 29 wherein the RF electric field is symmetric waveform that is generated through a second set of electrodes that generate an electric field that is substantially normal to that of the asymmetric electric field.

33. A method for separating ions comprising: introducing ions into an ion mobility based spectrometer; transporting and/or separating ions while supplying energy to the ions maintaining them at an energy level that is higher than the thermal energy at a given operating temperature; and preventing ions from continuously staying at the thermal energy level for substantially greater than 1 µs throughout the transportation and/or separation process.

34. The method of claim 33, wherein the energy level is controlled and/or adjusted to different levels for a sequence of ion mobility measurements.

35. The method of claim 33, further comprises preventing ions from and/or alter the degree of ions clustering with surrounding neutral molecules.

36. The method of claim 33, further comprises preventing ions from and/or alter the degree of ions clustering with surrounding neutral molecules in the ionization region and/or the chemical reaction regions.

37. The method of claim 33, wherein providing the energy by a RF electric field.

38. The method of claim 33, further comprises superimposing a symmetric RF electric field on an asymmetric waveform.

39. The method of claim 33, wherein the RF electric fields magnitude that is relatively constant in time by generating an RF electric field that rotates as a result of superposition of fields generated by different electrodes and RF drivers.

40. The method of claim 39, wherein the RF drivers operate at the same frequency but with different phases.

41. The method of claim 36, wherein the RF electric fields operate at different frequencies from different sources.

42. The method of claim 36, wherein the RF electric fields are substantially uniform in space by the use of multiple segmented guard electrodes driven with waveforms that have been phase shifted with respect to one another.

43. A method for separating ions comprising: introducing ions into an ion mobility based spectrometer; and transporting and/or separating ions while supplying energy to the ions maintaining them at an energy level that is higher than the thermal energy at a given operating temperature, the ions continuously staying at the elevated level throughout the separation process, the ionization process and/or the chemical reaction process.

* * * * *